US011380079B2

(12) United States Patent
    Caluser

(10) Patent No.: US 11,380,079 B2
(45) Date of Patent: Jul. 5, 2022

(54) SYSTEM AND METHOD FOR POSITIONAL REGISTRATION OF MEDICAL IMAGE DATA

(71) Applicant: Metritrack, Inc., Hillside, IL (US)

(72) Inventor: Calin Caluser, Glen Ellyn, IL (US)

(73) Assignee: Metritrack, Inc., Hillside, IL (US)

( * ) Notice: Subject to any disclaimer, the term of this patent is extended or adjusted under 35 U.S.C. 154(b) by 1129 days.

(21) Appl. No.: 15/551,354

(22) PCT Filed: Feb. 18, 2016

(86) PCT No.: PCT/US2016/018379
§ 371 (c)(1),
(2) Date: Aug. 16, 2017

(87) PCT Pub. No.: WO2016/134093
PCT Pub. Date: Aug. 25, 2016

(65) Prior Publication Data
US 2018/0046875 A1 Feb. 15, 2018

Related U.S. Application Data

(60) Provisional application No. 62/176,411, filed on Feb. 19, 2015.

(51) Int. Cl.
*G06T 7/33* (2017.01)
*A61B 5/00* (2006.01)
(Continued)

(52) U.S. Cl.
CPC .......... *G06V 10/245* (2022.01); *A61B 5/0077* (2013.01); *A61B 5/055* (2013.01);
(Continued)

(58) Field of Classification Search
CPC . A61B 2676/00; A61B 5/0077; A61B 5/4887; A61B 6/025; A61B 6/584;
(Continued)

(56) References Cited

U.S. PATENT DOCUMENTS 5,668,844 A * 9/1997 Webber .................. A61B 6/025
                                                   378/162
6,122,541 A * 9/2000 Cosman ................. A61B 90/10
                                                   600/426
(Continued)

FOREIGN PATENT DOCUMENTS

WO  WO-2013101562 A2 *  7/2013  .......... A61B 8/4263
WO     2014099825 A2     6/2014

OTHER PUBLICATIONS

Wikipedia Entry for "fiducial marker" (https://web.archive.org/web/20150211164211/http://en.wikipedia.org/wiki/Fiducial_marker) from Feb. 11, 2015 (Year: 2015).*
Madan et al., "Multimodal and Time-Lapse Skin Registration," Skin Research and Technology, 2014, John Wiley & Sons Ltd., pp. 1-8.

*Primary Examiner* — Boniface Ngathi N
*Assistant Examiner* — Milton Truong
(74) *Attorney, Agent, or Firm* — Vedder Price P.C.

(57) ABSTRACT

A system and method of correlating or coregistering medical images is disclosed herein that includes acquiring a surface image of the patient's skin surface using a surface detector assembly comprising a surface frame and a camera system registered to the surface frame. Positional coordinates of one or more surface landmarks in the surface image are determined and a medical image of the patient is acquired having the surface frame depicted therein. A second surface image of the patient's skin surface is acquired that at least partially overlaps the previously acquired surface image. Positional coordinates of one or more surface landmarks in the second surface image are determined and compared with surface landmarks in the previous surface image. Common surface landmarks are determined based on the comparison and the medical images are coregistered based on positional coordinates of the common surface landmarks.

21 Claims, 17 Drawing Sheets

(51) Int. Cl.
  *G06V 10/24* (2022.01)
  *A61B 6/02* (2006.01)
  *A61B 6/03* (2006.01)
  *A61B 6/00* (2006.01)
  *A61B 5/055* (2006.01)
  *A61B 8/00* (2006.01)
  *A61B 8/08* (2006.01)

(52) U.S. Cl.
  CPC .............. *A61B 6/025* (2013.01); *A61B 6/032* (2013.01); *A61B 6/502* (2013.01); *A61B 6/5247* (2013.01); *A61B 6/584* (2013.01); *A61B 8/4245* (2013.01); *A61B 8/5261* (2013.01); *G06T 7/33* (2017.01); *A61B 5/0071* (2013.01); *A61B 5/441* (2013.01); *A61B 5/489* (2013.01); *A61B 5/4887* (2013.01); *A61B 5/7207* (2013.01); *A61B 2576/00* (2013.01); *G06T 2207/30004* (2013.01); *G06T 2207/30204* (2013.01)

(58) Field of Classification Search
  CPC .. A61B 8/4245; G06K 9/3233; G06K 9/3216; G06K 9/3241; G06T 2207/30088
  See application file for complete search history.

(56) References Cited

U.S. PATENT DOCUMENTS

| | | | |
|---|---|---|---|
| 8,463,006 B2 | 6/2013 | Prokoski | |
| 2008/0219528 A1* | 9/2008 | Edgar | B41J 3/4073 |
| | | | 382/128 |
| 2009/0124906 A1* | 5/2009 | Caluser | G16H 30/20 |
| | | | 600/443 |
| 2010/0080417 A1* | 4/2010 | Qureshi | A61B 34/10 |
| | | | 382/103 |
| 2010/0172567 A1* | 7/2010 | Prokoski | A61B 5/0064 |
| | | | 382/132 |
| 2010/0259272 A1 | 10/2010 | Care | |
| 2011/0134113 A1 | 6/2011 | Ma et al. | |
| 2012/0130234 A1* | 5/2012 | O'Connor | A61B 6/0414 |
| | | | 600/427 |
| 2013/0070980 A1 | 3/2013 | Hyde et al. | |
| 2013/0296707 A1* | 11/2013 | Anthony | A61B 8/13 |
| | | | 600/459 |
| 2014/0031664 A1 | 1/2014 | Kang et al. | |
| 2014/0355840 A1* | 12/2014 | Pearson Peyton | G06T 7/0014 |
| | | | 382/115 |
| 2015/0051489 A1* | 2/2015 | Caluser | A61B 8/0825 |
| | | | 600/440 |

* cited by examiner

SYSTEM AND METHOD FOR POSITIONAL REGISTRATION OF MEDICAL IMAGE DATA

CROSS REFERENCE TO RELATED APPLICATION

The present invention claims the benefit of U.S. Provisional Patent Application Ser. No. 62/176,411, filed Feb. 19, 2015, the disclosure of which is incorporated herein by reference in its entirety.

BACKGROUND OF THE INVENTION

Embodiments of the invention relate generally to medical imaging and, more particularly, to a system and method for system for coregistering medical images based on the detected location of surface landmarks located on or near the skin surface.

The registration of different sets of body or medical images has important diagnostic and therapeutic uses. Two or more different sets of medical images of same body region acquired during different examinations or at different times can be registered together to display same location in different sets of images. The body registration with previous sets of medical images is used for surgical instrument navigation, co-registration of one or more sets of clinical images like CT, MRI with images obtained in real time with handheld imaging probes like ultrasound probes, gamma camera probes among others. The registration process relies on matching the position of multiple common points or regions contained in a previous set of images with the body, real time images or a different set of images.

The current methods for image coregistration use external fiducial markers or reproducible body landmarks to coregister one image set with another image set or with the body. However, the co-registration accuracy and precision between different image sets or between an image set and the body is limited due to the poor positional reproducibility of the attached fiducial markers, when needed to be reattached for a different set of image acquisition. In imaging techniques that use reproducible body landmarks for coregistration, body landmarks such as the umbilicus, bony structures, nipple of the breast or common internal structures such as vessel crossings are detected within the medical images. The accuracy and ease of registering medical images using body landmarks is limited by the irregular shape and large size of the available landmarks, as well as the low number of these landmarks that can be detected within medical images.

Patient body motion also creates another source of registration error between sets of medical images, which can significantly degrade the navigation accuracy of medical instruments or the image fusion or correlation of different sets of medical images.

The imaging of deformable body parts, like the breast, takes place with the body part deformed in different shapes and positions, which makes the co-registration of different sets of images difficult or impossible. For example, the breast is compressed medial to lateral and top to bottom with the patient standing to obtain mammographic or tomosynthesis images, the breast is compressed medial to lateral with the patient prone to obtain breast MRI images and not compressed with the patient supine for free hand ultrasound imaging. Multiple mathematical models have been studied to perform the co-registration of images obtained with different modalities, however so far limited success was achieved for clinical applications. Adding common reproducible body landmarks with known position, such as the nipple, to the mathematical algorithms can improve the results of registering images of body parts with different deformation. However, the usefulness of these techniques is limited due to the small number of reproducible body landmarks and the unreliability of detection of these body landmarks within the medical images.

As a result, it would be desirable to have an apparatus and method of coregistering medical images that accounts for patient body motion and that is capable of coregistering images with a higher degree of accuracy than existing prior art systems. It would also be desirable for such an apparatus and method to be useable to coregister images of deformable body parts, such as the breast.

BRIEF DESCRIPTION OF THE INVENTION

The invention is directed to a system and method for coregistering medical images using surface landmarks detected in images acquired of the skin surface of a medical patient.

In accordance with one aspect of the invention, a system for coregistering medical images includes a surface detector assembly positionable on a skin surface of a medical patient. The surface detector assembly includes a surface frame and a camera system coupled to the surface frame and configured to acquire surface images of a portion of the skin surface of the medical patient positioned proximate a lower surface of the surface frame. The system also includes a processor having a surface frame image module connected to a signal output of the camera system and programmed to identify positional coordinates of at least one common surface landmark within the acquired surface images. The processor also includes a coregistration module programmed to co-register a first medical image of the medical patient with a second medical image of the medical patient based on the positional coordinates of the at least one common surface landmark identified by the surface frame image module, positional coordinates of the surface frame within the first medical image, and positional coordinates of the surface frame within the second medical image. A display module generates a display of the at least one common surface landmark relative to the surface frame on a body diagram of the medical patient.

In accordance with another aspect of the invention, a method of coregistering medical images includes acquiring a first surface image of a first skin surface of a medical patient using a surface detector assembly comprising a surface frame coupleable to the skin surface and a camera system registered to the surface frame. The method also includes determining positional coordinates of at least one surface landmark in the first surface image, acquiring a first medical image of the medical patient having the surface frame depicted therein, and acquiring a second surface image of a second skin surface of the medical patient, the second skin surface at least partially overlapping the first skin surface. The method further includes determining positional coordinates of at least one surface landmark in the second surface image, comparing the at least one surface landmark in the first surface image to the at least one surface landmark in the second surface image, identifying at least one common surface landmark based on the comparison, and coregistering the first medical image with the second medical image based on positional coordinates of the at least one common surface landmark.

In accordance with a further aspect of the invention, a non-transitory computer readable storage medium has stored thereon instructions that cause a processor to access a first medical image of a medical patient having a first surface frame depicted at a first position on the medical patient, access a first surface image acquired of a skin surface of a medical patient beneath the first surface frame, and detect surface landmarks within the first surface image. The instructions further cause the processor to access a second medical image of the medical patient having a second surface frame depicted at a second position on the medical patient, the second position at least partially overlapping the first position, access a second surface image acquired of a skin surface of a medical patient beneath the second surface frame, and detect surface landmarks within the second surface image. The instructions further cause the processor to compare the surface landmarks within the first surface image to the surface landmarks within the second surface image, identify at least one common surface landmark within the first surface image and the second surface image based on the comparison, and coregister the first medical image with the second medical image based on positional coordinates of the at least one common surface landmark.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Initially, it is to be understood that the embodiments of the invention described herein are not limited in application to the details of arrangements of the components set forth in the following description. As will be appreciated by those skilled in the art, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Embodiments of the present invention address the above limitations and rely on the automatic detection of multiple surface landmarks at the body surface, otherwise difficult or impossible to detect by the visual inspection of the body surface or corresponding medical images. Superficial body landmarks can be reproducible skin texture patterns, including patterns not visible to the naked eye, moles, scars, superficial blood vessels or any other superficial reproducible marks which are different enough from other superficial patterns or marks to reliably allow their individual detection repeatedly. The body surface landmarks can be numerous, small and difficult or impossible to detect or distinguish by direct visual inspection of the skin or in the medical images. However, the surface landmarks can be automatically detected with the help of dedicated devices and can be used alone or in combination with other landmarks. By adding small multiple common landmarks to the registration of multiple sets of images or images with the body, the accuracy and precision of the registration can be improved.

Figure 1:
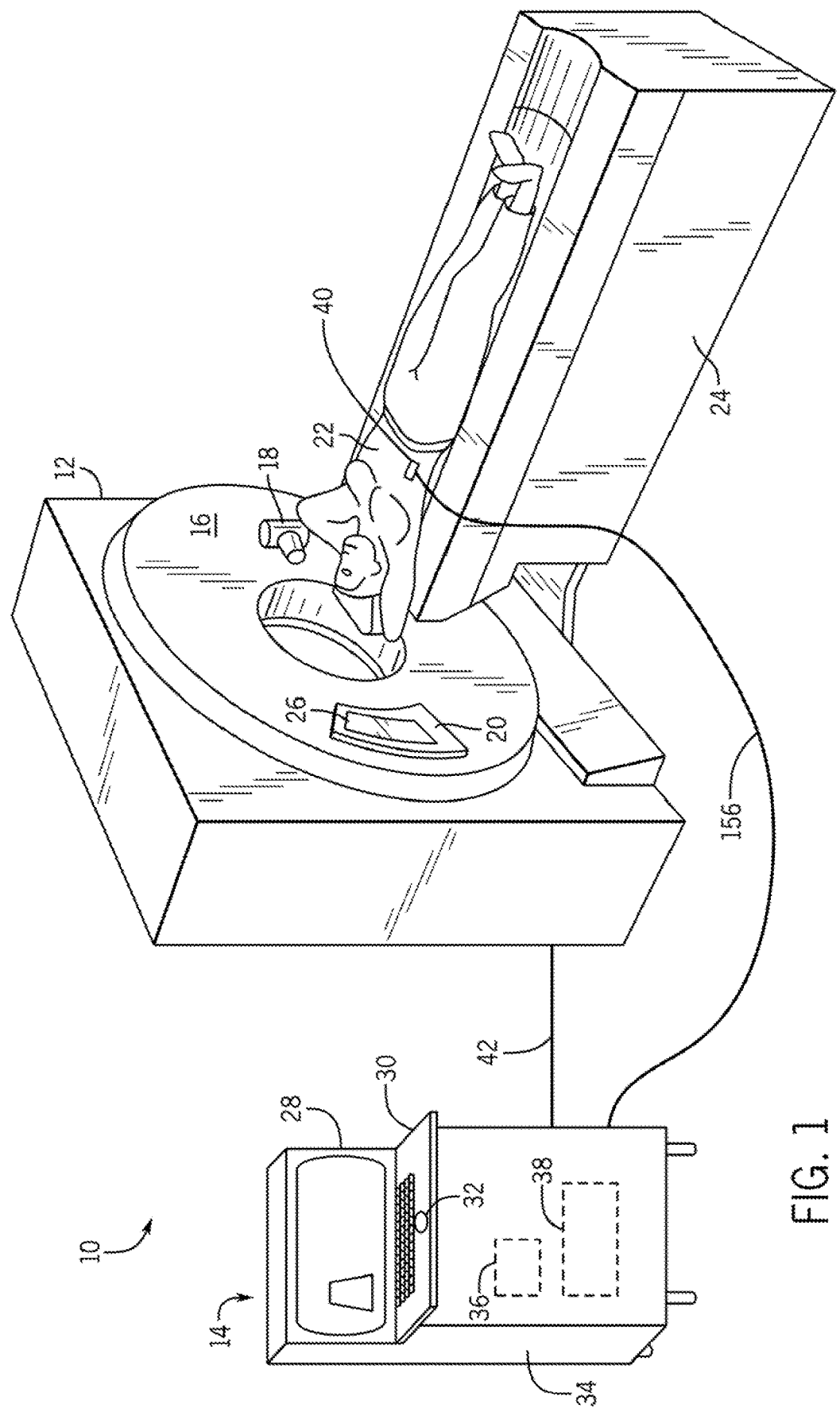
FIG. 1 depicts an overview illustration of an imaging system that includes a medical imaging device and an image coregistration system, according to an embodiment of the invention.

Turning to FIG. 1, a schematic illustration of an imaging system 10 is shown according to an embodiment of the invention. Imaging system 10 includes at least one medical imaging device 12 and an image coregistration system 14 with dedicated surface detector assembly 40. In the illustrated embodiment, medical imaging device 12 is an x-ray or computed tomography (CT) device, which includes a gantry 16 having an x-ray source 18 that projects a beam of x-rays toward a detector assembly or collimator 20 on the opposite side of the gantry 16. Individual detectors (not shown) within the collimator 20 sense the projected x-rays that pass through a medical patient 22 positioned on a table 24. A data acquisition system (DAS) 26 converts the data to digital signals for subsequent processing and eventual image reconstruction.

While FIG. 1 illustrates a CT device, it is contemplated that the medical imaging device 12 included in imaging system 10 may be an alternative imaging modality configured to acquire sectional medical images such as, for example, an x-ray system, a magnetic resonance imaging (MRI) system, a single-photon emission computed tomography (SPECT) imaging system, or an ultrasound system. According to yet other embodiments, imaging system 10 may include a combination of multiple, different imaging modalities such as, for example, an ultrasound system in combination with a CT system or an MRI system. Medical images separately acquired using any of these modalities may be co-registered in space relative to detected surface landmarks using the techniques described below.

The medical images acquired using medical imaging device 12 are accessed by image coregistration system 14, which includes a display 28, user interface with keyboard 30 and pointer 32, and a computer chassis 34 containing operating hardware, which is referred to hereafter as a processor 36, having programmed thereon software that coregisters multiple sets of medical images based on surface landmarks detected within surface images (described in detail below). Image coregistration system 14 includes a storage device 38, which may be contained within chassis 34 or provided as a standalone storage unit in alternative embodiments. Image coregistration system 14 also includes a dedicated surface detector assembly 40, described in more detail with respect to FIGS. 2-5, which detects surface landmarks located on the skin surface of the medical patient 22.

Figure 7:
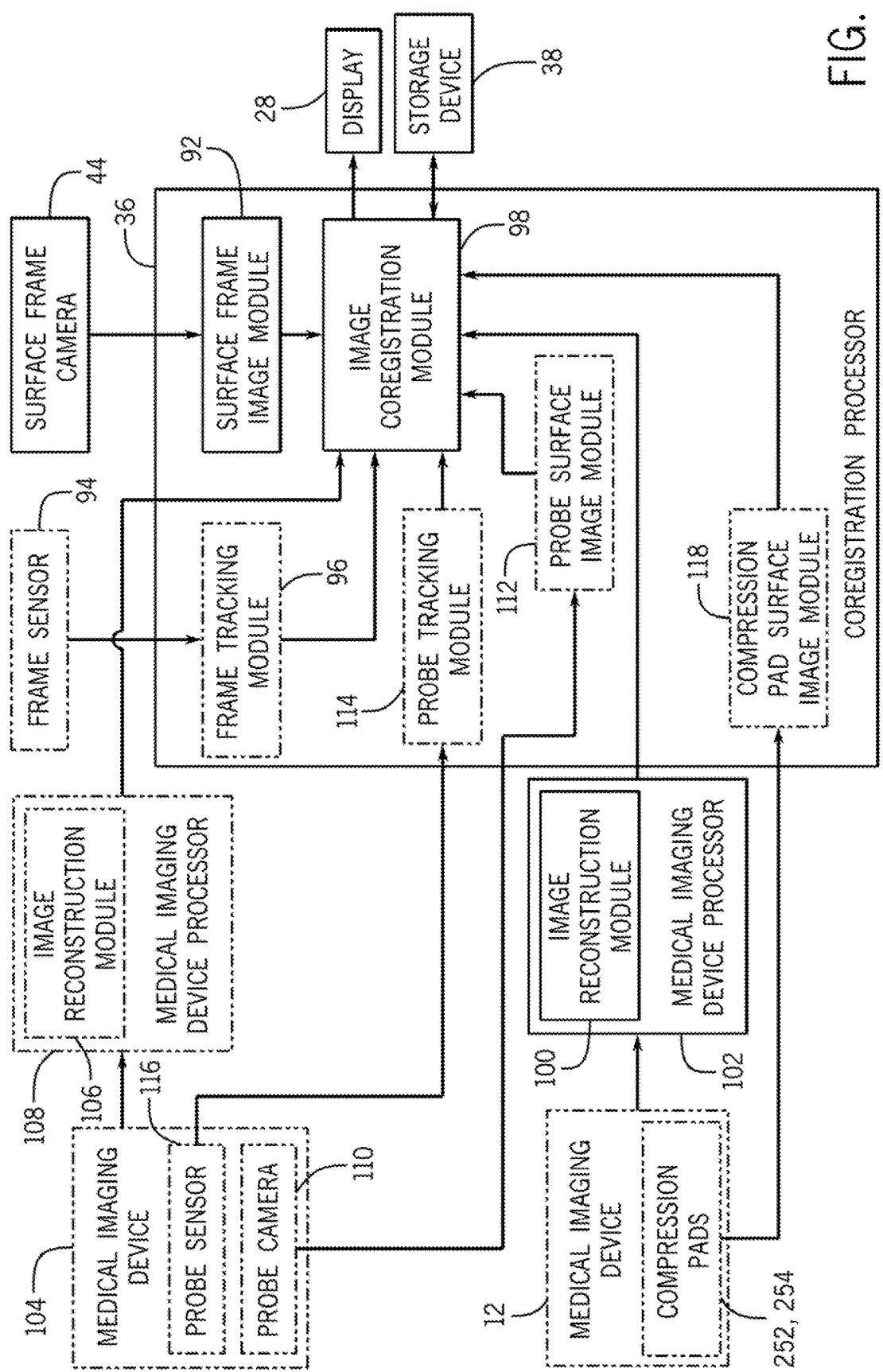
FIG. 7 is a functional block diagram of the imaging system of FIG. 1.

Processor 36 is provided with a number of modules, described in detail in FIG. 7, which are programmed with software that is used to process the data received by the processor 36 from surface detector assembly 40 and data received from medical imaging device 12. Processor 36 is also programmed with software to carry out the techniques discussed with respect to FIGS. 8, 9, 12, 14, and 16. In an alternative embodiment, processor 36 may also be programmed with image reconstruction software that would permit image coregistration system 14 to receive data directly from the medical imaging device 12 and reconstruct medical images therefrom.

In the illustrated embodiment, image coregistration system 14 is coupled to the medical imaging device 12 by way of a wired connection 42, however, it is contemplated that image coregistration system 14 may access the image data acquired by medical imaging device 12 wirelessly or through an external database otherwise coupled to medical imaging device 12.

Figure 2:
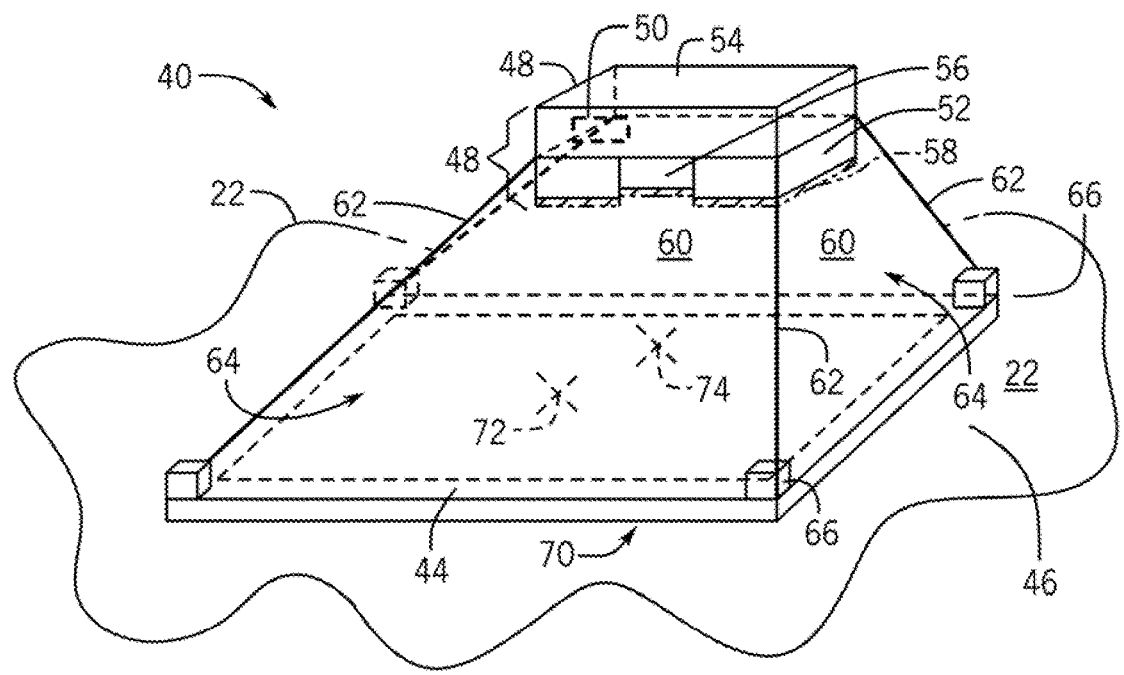
FIG. 2 is a schematic diagram of a surface frame and optional surface camera usable with the imaging system of FIG. 1, according to an embodiment of the invention.

Referring now to FIG. 2, surface detector assembly 40 is illustrated in additional detail. As shown, surface detector assembly 40 includes a surface frame 44 configured to be attached to the skin surface 46 of the medical patient 22. Surface frame 44 is attached to the skin surface 46 during the acquisition of medical images using medical imaging device 12 (FIG. 1) and is included in the medical images. As described in detail below, surface detector assembly 40 has the ability to detect surface landmarks on the skin surface 46 that are located within surface frame 44. In one exemplary and non-limiting embodiment, surface frame 44 is approximately three inches by three inches. However, it is contemplated that other frame sizes may be used as well.

Surface detector assembly 40 is designed to enable the detection of micro-features on or directly beneath the skin surface, including, for example, wrinkles, pores, other skin texture features, or veins visible through the skin surface. Surface detector assembly 40 includes a high-resolution camera system 48 having an image processor 50 for obtaining surface images of the skin surface 46 located beneath the surface frame 44, which can be processed and recorded. According to one embodiment, camera system 48 is integrated within the surface frame 44 and includes one or more light sources 52, one or more light detectors 54 with an optical portion or lens 56 that forms a surface image at the detectors 54 and generates a skin surface image that can be saved or transmitted to camera processor 50. Lens 56 is configured to produce magnified images at close range, such as, for example 2× and 4× magnification, to enable camera system 48 to be mounted on the surface frame 44 and used to detect skin micro-features. An optional filter 58 (shown in phantom) may be coupled to lens 56 or light source 52. Camera system 48 may be configured to operate light source(s) 52 to obtain skin surface images with one type of light, for example reflected polarized, visible light, or fluorescence mode (UVA), or obtain multimodal images using a combination of two or more light types. Additionally, the skin surface images can be enhanced by operating light source(s) 52 to illuminate the skin surface 46 with light of specific wavelengths in the visible or invisible spectrum.

In the illustrated embodiment, camera system 48 is attached to surface frame 44 with a standoff structure 60 that positions the lens 56 at a fixed position in reference to surface frame 44. The area between adjacent pillars 62 of the standoff structure 60 may be covered with a material 64 that is opaque to light to prevent the interference of ambient light with the light generated by light source 52 when taking surface images. Camera system 48 may also include an optional locking mechanism 66 (shown in phantom) that allows camera system 48 to be attached or detached from the surface frame 44. In an alternative embodiment, camera system 48 is a standalone device that couples to and is detachable from surface frame 44. Because the camera system 48 is fixedly positioned with respect to surface frame 44, surface images acquired with camera system 48, and the position of surface landmarks contained therein, are registered to the surface frame 44. In other embodiments multiple cameras can be used with surface frame 44 or one or more cameras that can move in reference to surface frame 44 can be used to obtain a whole picture of the surface bordered by surface frame 44.

Surface frame 44 is firmly attached to the skin surface 46 of the medical patient 22 with a detachable coupling material 68 (FIG. 5), such as, for example, medical tape or medical glue, which can be removed after an examination. In the illustrated embodiment, the lower surface 70 of the surface frame 44 is flat and camera system 48 generates a two-dimensional image of the skin surface 46. In an alternative embodiment, the lower surface 70 of surface frame 44 may be configured having a curved, non-flat profile to align with the body contour and permit camera system 48 to generate stereoscopic images of the skin surface 46.

In one embodiment of the invention, camera processor 50 or processor 36, is programmed with one or more pattern recognition algorithms designed to process the acquired skin surface images and detect one or more surface landmarks 72, 74 located at the skin surface 46 within the surface frame 44. In an alternative embodiment, processor 36 of computer 34 may be programmed having one or more pattern recognition algorithms. According to various embodiments, camera processor 50 or processor 36 may be programmed with an algorithm that detects surface skin patterns and marks with visible or invisible light similar to that disclosed in U.S. patent application Ser. No. 13/798,899 or Multimodal and Time-lapse Skin Registration, S. Madan, K. J. Dana and G. O. Cula, Skin Research and Technology 2014; 0:1-8. Alternatively, the location of other body surface features, such as superficial, small veins located beneath the skin surface 46 within the surface frame 44, can be captured using near infrared light, processed via camera processor 50 and recorded. In such an embodiment, a vein viewing product such as one produced by Accuvein company of Huntington, New York may be used. In yet another embodiment, the surface landmarks 72, 74 or other body surface features within surface frame 44 can be manually detected and marked in the images obtained with camera system 48.

Figure 3:
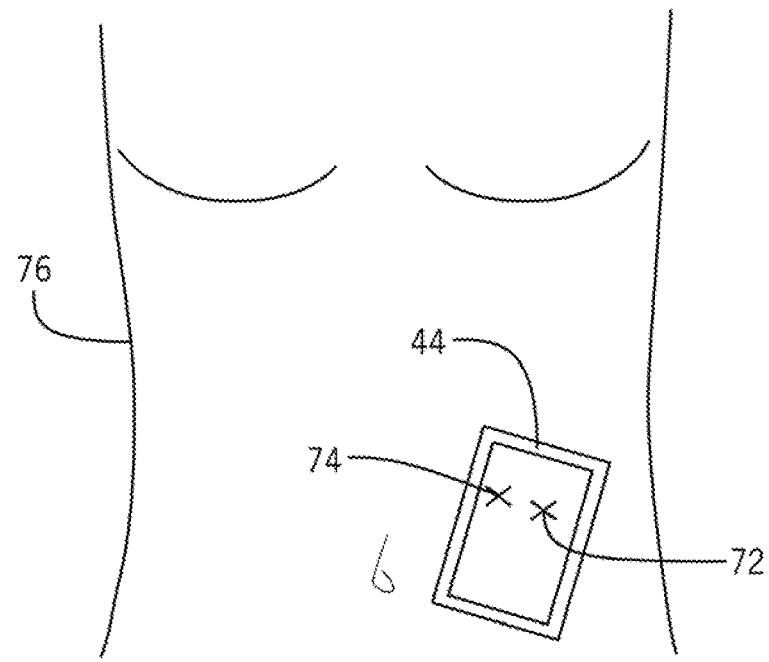
FIG. 3 is an exemplary body diagram that schematically illustrates the position of the surface frame of FIG. 2 with respect to detected surface landmarks.

Once detected, the locations of surface landmarks 72, 74 or other body surface features are stored by camera processor 50 or processor 36, according to alternative embodiments. The location of surface landmarks 72, 74 and surface frame 44 also may be displayed to an operator on a body diagram 76 of the medical patient 22, as shown in FIG. 3. The size and shape of the surface frame 44 is known and can be registered with the obtained surface images. Therefore, after a given skin surface image is registered with the surface frame 44, the position of all pixels in the skin surface image is known in reference to the surface frame 44.

Figure 4:
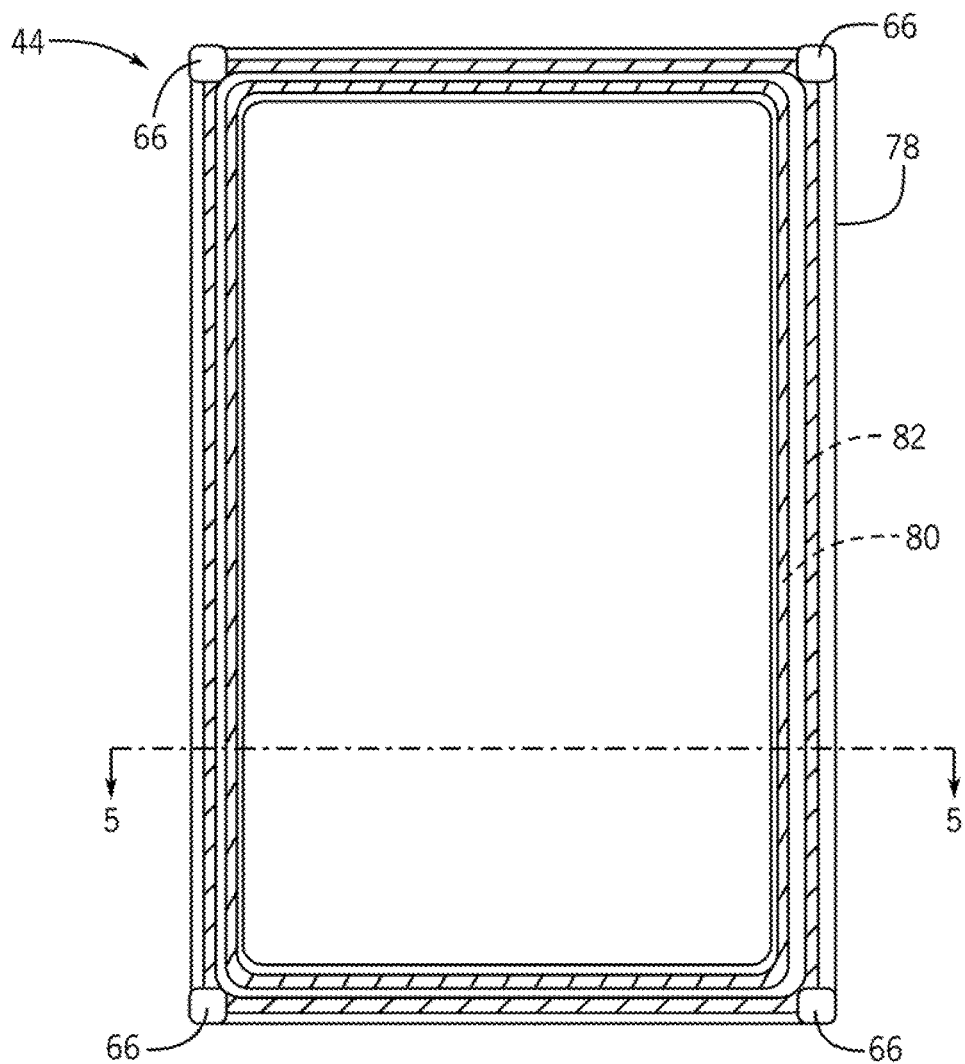
FIG. 4 is a top view of the surface frame of FIG. 2, according to an embodiment of the invention.
Figure 5:
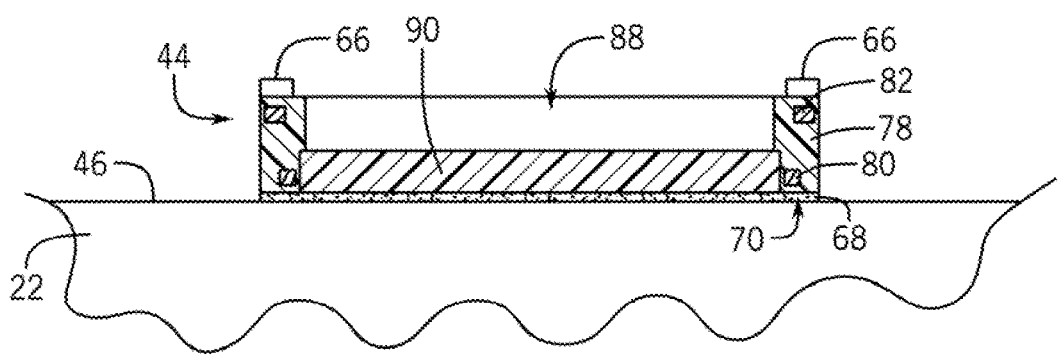
FIG. 5 is a cross-sectional view of FIG. 2.

As described in more detail below with respect to the technique set forth in FIG. 8, the surface frame 44 is attached to the skin surface 46 prior to a medical imaging procedure and, therefore, is detectable in the obtained medical images. As such, surface frame 44 can be constructed specifically for a given imaging modality, or can be constructed for multi-modality use. A top view of a surface frame 44 constructed for multi-modality use is illustrated in FIG. 4. Surface frame 44 includes an outer shell 78 constructed using a biocompatible material such as polyurethane. Embedded within the outer shell 78 is a radiopaque material 80, such as, for example, a metallic wire or tube with barium sulphate, which is detectable using a CT imaging device. Oil-filled tubing 82 or capsules, detectable by a MIII imaging device, is also embedded within the outer shell 78. In one embodiment, radiopaque material 80 and oil-filled tubing 82 are positioned adjacent each other within surface frame 44, as shown in the cross-sectional view provided in FIG. 5. In an alternative embodiment shown in FIG. 6, radiopaque material 80 is positioned in the center of oil-filled tubing 82. In single modality embodiments, surface frame 44 is constructed to include a material detectable by the given imaging modality.

Figure 6:
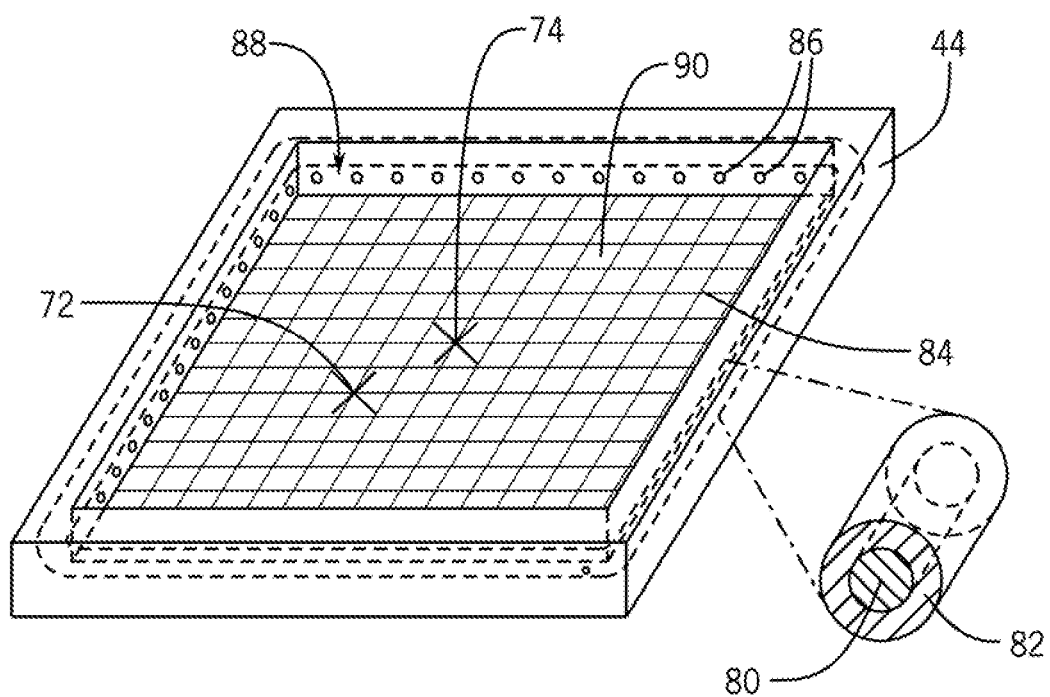
FIG. 6 is a perspective view of the surface frame of FIG. 2, according to an embodiment of the invention.

A perspective view of surface frame 44 is illustrated in FIG. 6 and illustrates a grid 84 of visible lines, which can be incorporated in surface frame 44 to aid the localization of the surface landmarks 72, 74 detected with the camera system 48. In one embodiment, grid 84 is formed of intersecting light beams generated from a matrix of light sources 86, such as, for example laser emitting LEDS, which are integrated within the surface frame 44. In an alternative embodiment, grid 84 is constructed of a radiopaque material, such as, for example thin metallic wires, which extend across the length and width of the opening 88 within surface frame 44 and are detectable in the medical images. Optionally, a transparent plate or pad 90 can be positioned within the opening 88 of surface frame 44 to compress the underlying skin. In such an embodiment, the visible grid 84 can be incorporated in the transparent plate or pad 90.

Referring now to FIG. 7, a functional block diagram illustrating the various general working aspects of imaging system 10 of FIG. 1 is shown. Surface images acquired by camera system 48 are processed within a surface frame image module 92 that detects the surface landmarks 72, 74 on the skin surface 46 and determines the relative position of the surface landmarks 72, 74 with respect to the surface frame 44. In embodiments that include one or more optional position sensor(s) 94 located on surface frame 44, positional data from position sensors 94 is received by a frame tracking module 96 or board of the processor 36, which processes the received data and provides the data to an image coregistration module 98 of processor 36. As described in additional detail below with respect to FIGS. 9 and 11, optional position sensor(s) 94 may be used to reposition the surface frame 44 during a subsequent examination and to track movement of the body of the medical patient 22 for dynamic image coregistration in embodiments that utilize a handheld imaging probe or surgical implement. Surface frame image module 92 outputs the positional coordinates of the surface landmarks 72, 74 to an image coregistration module 98. Image coregistration module 98 can access previously acquired and stored image sets with corresponding surface landmarks positions from storage device 38, coregister the stored image sets with the body of medical patient 22 and/or a current set of images, or coregister two or more sets of previously acquired images based on the positional coordinates of corresponding surface landmarks. Image data acquired by medical imaging device 12 is reconstructed into medical images within an image reconstruction module 100 of the processor 102 of medical imaging device 12. The position of surface frame 44 relative to the medical images acquired using medical device 12 is determined in the medical image set where the surface frame 44 is included and visualized, and image coregistration module 98 subsequently calculates the position of landmarks 72 and 74 relative to the medical images.

Optionally, image reconstruction module 100 may be coupled to an additional medical imaging device 104 (shown in phantom) each having an associated image reconstruction module 106 within its processor 108. According to various embodiments, the additional medical imaging device 104 may be an x-ray, CT, MRI, SPECT, or ultrasound imaging device. After the positional coordinates of one or more surface landmarks 72, 74 relative to a set of medical images acquired using additional medical imaging device 14 is calculated in a similar manner as for medical imaging device 12, medical images acquiring using devices 12, 14 can be coregistered by image coregistration module 98. Alternatively, different sets of medical images with surface landmarks obtained with same imaging device at different times can be coregistered by module 98. In embodiments where additional medical imaging device 104 is an ultrasound device, skin surface images acquired using a surface camera 110 coupled to the handheld imaging probe 214 of the ultrasound surface image module 112 or board of the processor 36. In embodiments where additional medical imaging device 104 is an ultrasound machine that generates analog images, an analog to digital video output module (not shown) is provided within processor 108 to digitize images received from the ultrasound machine 104. Image coregistration module 98 receives the digital ultrasound images from image reconstruction module 106, ultrasound probe positional data from a probe tracking module 114 coupled to a ultrasound position sensor 116, and surface image data with associated positional information of surface landmarks from probe surface image module 112.

Figure 17:
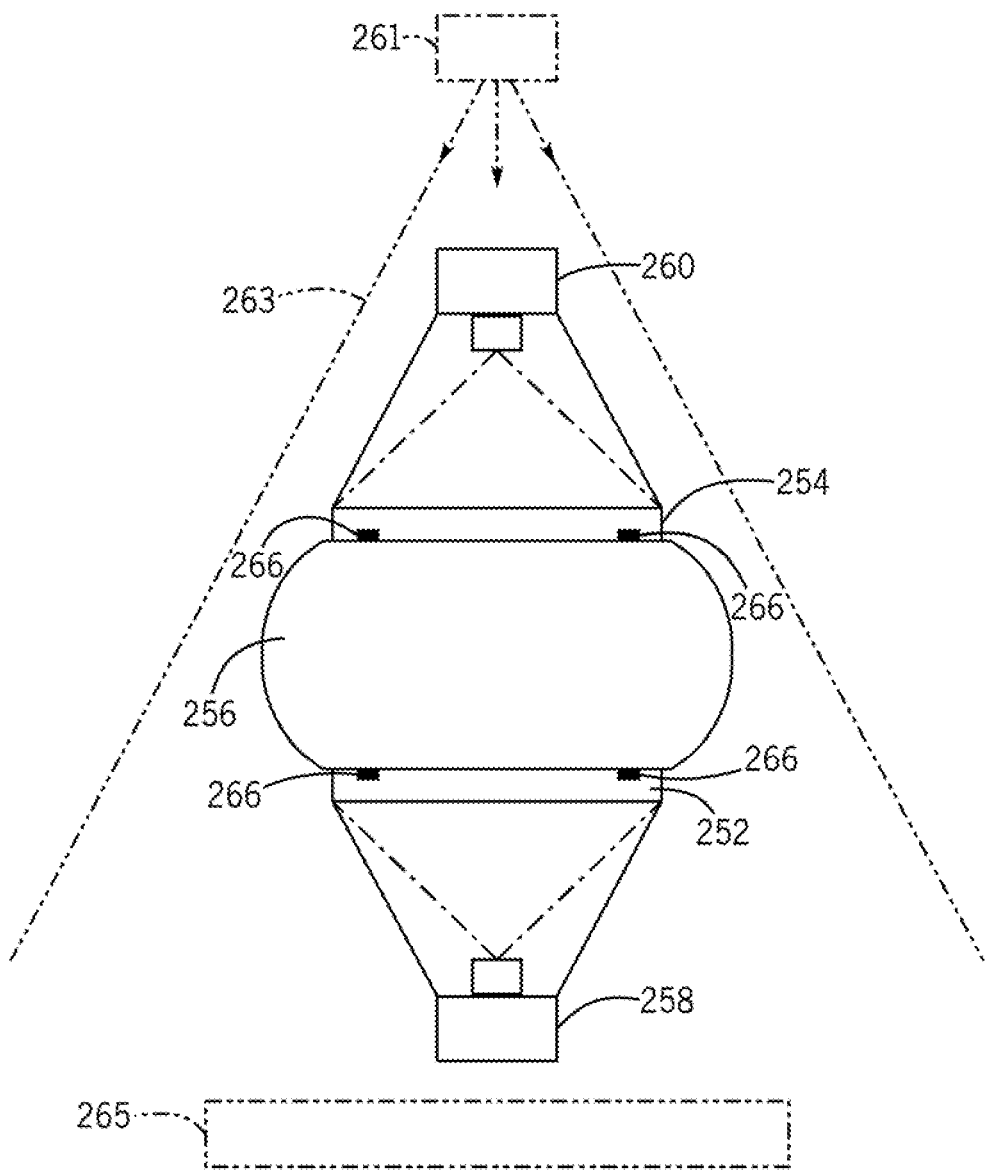
FIG. 17 is a schematic diagram of a compression pad useable with the image registration technique set forth with respect to FIG. 16, according to an embodiment of the invention.

In embodiments where medical imaging device 12 is a mammography machine that generates two- or three-dimensional images of the breast, medical imaging device 12 is also provided with compression pads 252, 254, the structure and function of which is described in additional detail with respect to FIG. 17. Skin surface image data acquired using compression pads 252, 254 is received by a compression pad surface image module 118 or board within processor 36, which processes surface images acquired using compression pads 252, 254 and outputs positional coordinates of detected surface landmarks to image coregistration module 98. While only one additional medical imaging device 104 is illustrated in FIG. 7, it is contemplated that more than one additional medical imaging device may be provided within imaging system 10.

As described in additional detail below, image coregistration module 98 uses the data received by image reconstruction module 100, surface frame image module 92, and optionally, frame tracking module 96, probe surface image module 112, and/or compression pad surface image module 118 to coregister multiple sets of medical images based on the positional coordinates of one or more surface landmarks 72, 74 detected in surface images acquired using surface frame camera system 48, ultrasound surface camera 110 and/or compression pads 252, 254. The coregistered images and associated coregistration data is output to a storage device 38 and/or displayed to a user on a display 28. The functionality of modules 92, 96, 98, 112, and 118 is described in more detail below.

Figure 8:
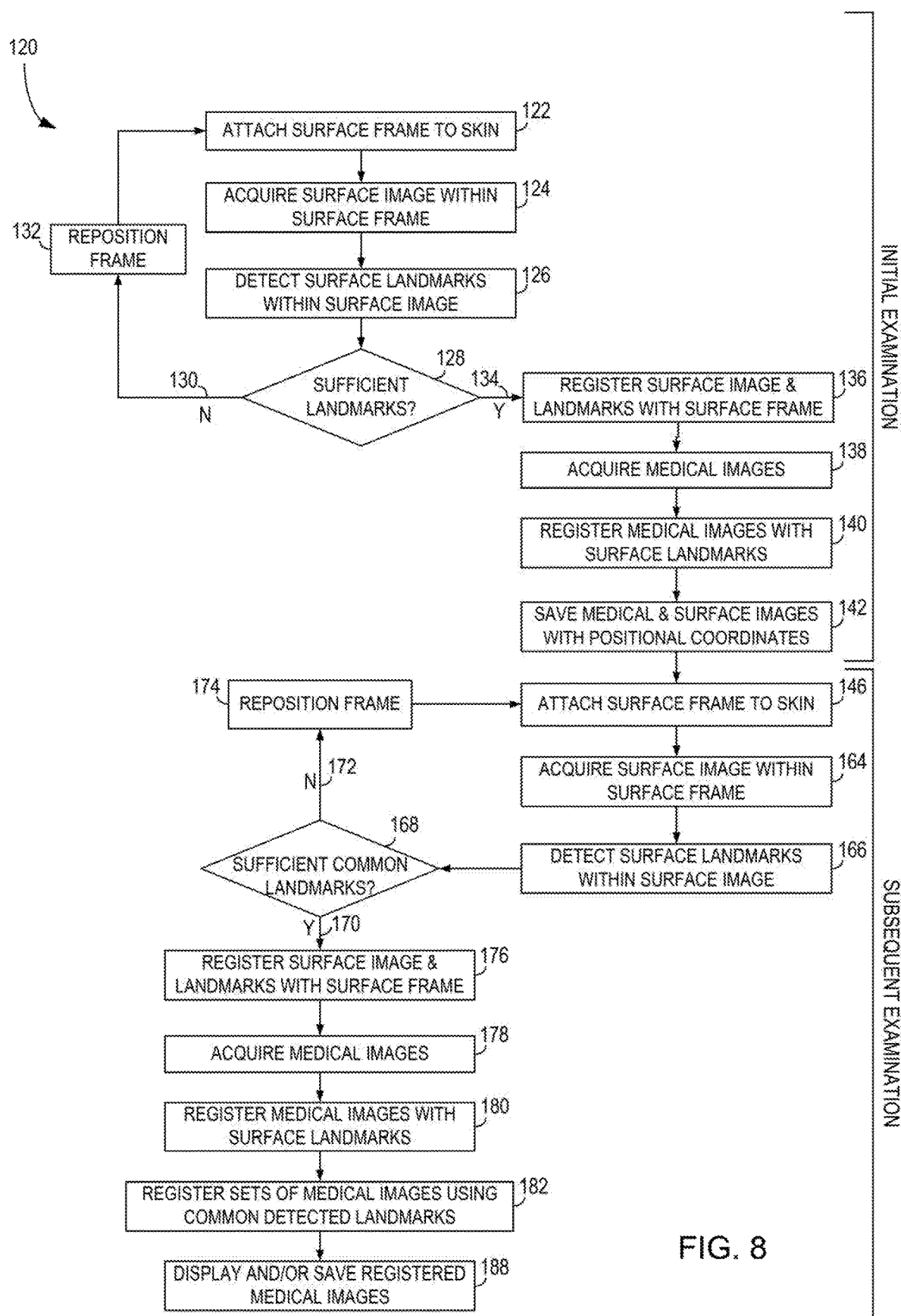
FIG. 8 is a flow chart illustrating the steps of a technique for registering sets of medical images using detected surface landmarks, according to an embodiment of the invention.

Referring now to FIG. 8, and with continued reference to FIGS. 1-7 as appropriate, an operating technique 120 for image coregistration system 14 is set forth that includes the steps for registering sets of medical images using detected surface or surface landmarks, according to an embodiment of the invention. At the beginning of an examination at step 122 the surface frame 44 is attached to the skin surface 46 of the medical patient 22. Camera system 48 is used to acquire surface images of the skin surface 46 within the surface frame 44 at step 124. Surface or surface landmarks 72, 74 within the acquired surface images are detected at step 126 and the position of the surface landmarks 72, 74 is registered with the surface frame 44. While only two surface landmarks 72, 74 are illustrated and described herein, it is contemplated that more than two surface landmarks may be detected in the surface images to improve accuracy and precision of the coregistration technique. Alternatively, it is contemplated that the image coregistration techniques described herein may be carried out using a single detected surface landmark 72 or 74 in embodiments that use multiple surface frames. At step 128 the technique 120 determines whether sufficient surface landmarks have been detected within the acquired surface images.

The surface images can be obtained at any time after the surface frame 44 is attached to the skin surface 46. In the embodiment illustrated in FIG. 8, the surface images are obtained prior to performing a medical imaging procedure and obtaining the medical images. Such an approach may be useful in the event that surface detector assembly 40 does not detect sufficient surface landmarks 72, 74 within the surface frame 44 at step-register medical and surface images 130. If this is the case, the surface frame 44 is repositioned at step 132 at a different location on the skin surface 46 prior to acquiring medical images. However, if sufficient landmarks are detected 134 within the surface frame 44, technique 120 proceeds to register the acquired surface images and associated detected surface landmarks with the frame at step 136.

Medical images of the medical patient 22 are acquired using the medical imaging device 12 at step 138. These medical images can be represented by cross-sectional images like CT, MRI, SPECT, or any other two-dimensional or three-dimensional images of the body of the medical patient 22. The attached surface frame 44 is included in the medical images and, therefore, its position relative to the body of the medical patient 22 is known. Because the previously obtained surface images within surface frame 44 are registered with the surface frame 44, the surface images subsequently can be registered with the body surface in the acquired medical images and the associated surface landmarks within those surface images using processor 36 at step 140. The positional coordinates of the surface frame 44 on the medical patient 22 is saved with the medical images at step 142.

To register one set of medical images of the body of the medical patient 22 to a second set of medical images of the body of the medical patient 22, one or more of the same or common surface landmarks must be identified in at least one surface image acquired in connection with both sets of medical images. To achieve this task, a surface frame 144 is applied to approximately same region of the skin surface 46 prior to acquisition of a set of medical images as surface frame 44 had been applied during acquisition of the previous set(s) of medical images. The surface frame 144 used to acquire skin surface images during the second examination is described below as having a different part number than the surface frame 44 used during the first examination for purposes of clarity. In some embodiments, different surface frames may be used to acquire skin surface images in different examinations. In such embodiments, surface frame 144 functions in an identical manner as described above with respect to surface frame 44. In alternative embodiments, the same surface frame 44 is used to acquire skin surface images during the first and second examinations.

Unlike prior art techniques that require the fiducials to be applied to exactly the same location and orientation on the patient body in order to coregister image sets, the surface frame 44, 144 need not be positioned identically from one image set to the next. Instead, surface frame 144 can be positioned in any orientation to the body and must only be positioned to partially overlap the location of the skin surface 46 on which surface frame 44 was positioned in the previous examination in order to permit detection of sufficient common surface landmarks on the skin surface 46. Because the surface frame 144 needs only to cover a portion of the area covered by the surface frame 44 in the previous imaging procedure, the size and shape of the surface frame 144 applied during the second examination procedure can differ from the size and shape of the surface frame 44 used during the first examination. In one embodiment, the surface frame 144 used for the second examinations is sized to be larger than the surface frame 44 used to acquire the first set of images so that less precision is required to ensure that surface frame 144 at least partially overlaps the skin surface covered by surface frame 44 during the previous examination. In other words, different frames may be used between examinations, thereby permitting images to be coregistered that were acquired using different surface detector assemblies. The larger the size of surface frames 44, 144 the better chances to detect more common surface landmarks and improve the coregistration of sets of medical images. However, the size of the surface frames 44, 144 is limited by the changes in the skin surface shape over the body, which limits the registration of surface points to the frames 44, 144.

Accordingly, at the beginning of a second or subsequent examination, technique 120 proceeds at step 146 by attaching the surface frame 144 to the skin surface 46 at approximately the same position at which surface frame 44 was positioned in a previous set of images. In one embodiment, the repositioning of the surface frame 144 over the same body surface at a different examination is done manually by observing the position of surface frame 44 in a previous exam and aligning the surface frame 144 using existing anatomical references, such as, for example the umbilicus, iliac crests, body orientation planes or other landmarks. In another embodiment, the registration of the surface frame 144 relative to the body is used to assist in realigning the surface frame 144 over approximately the same area of the skin surface during a subsequent examination.

Figure 9:
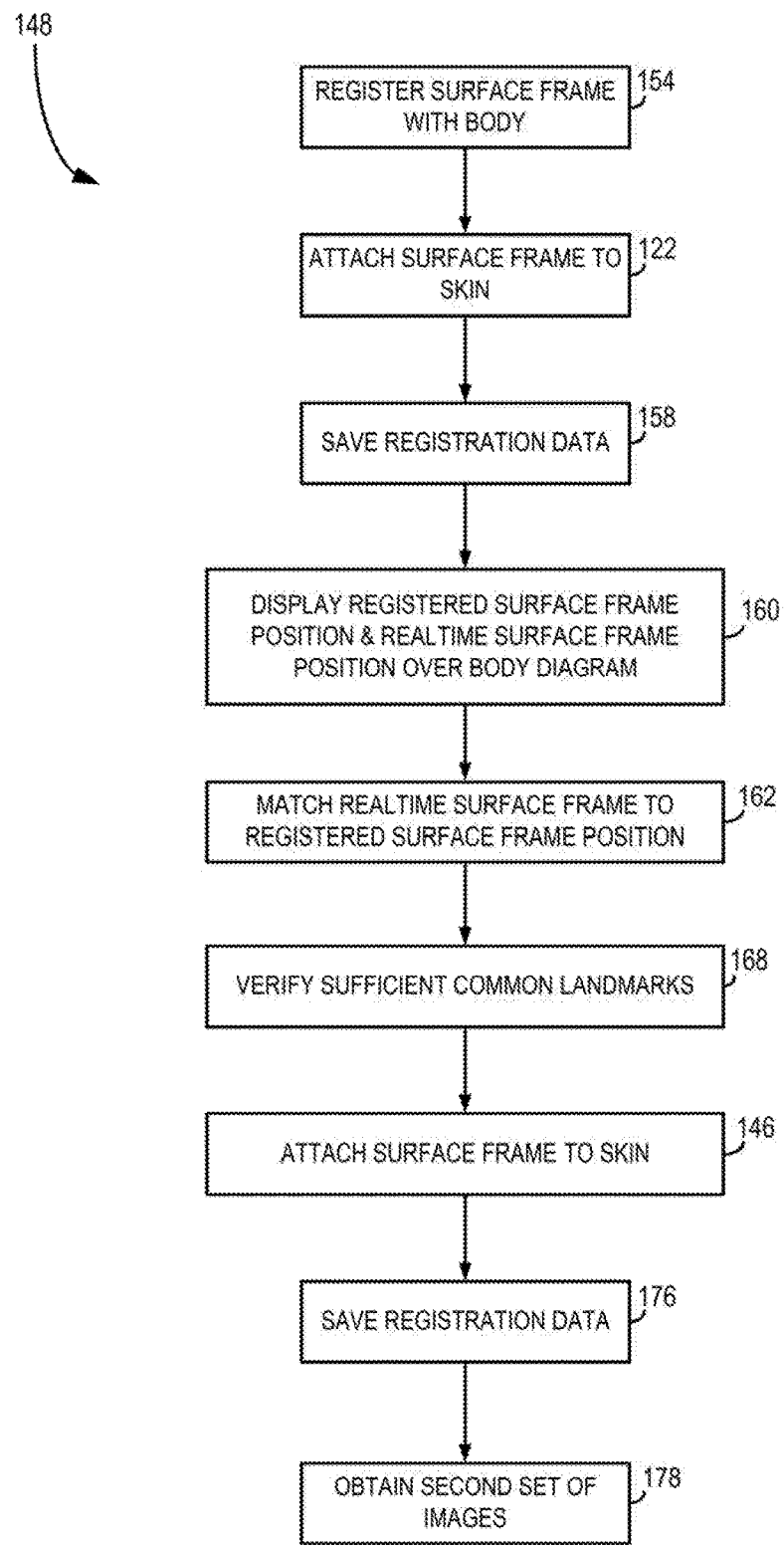
FIG. 9 is a flow chart illustrating the steps of a subroutine, usable with the technique set forth in FIG. 8, for repositioning a surface frame prior to acquisition of a second or subsequent set of medical images, according to an embodiment of the invention.
Figure 11:
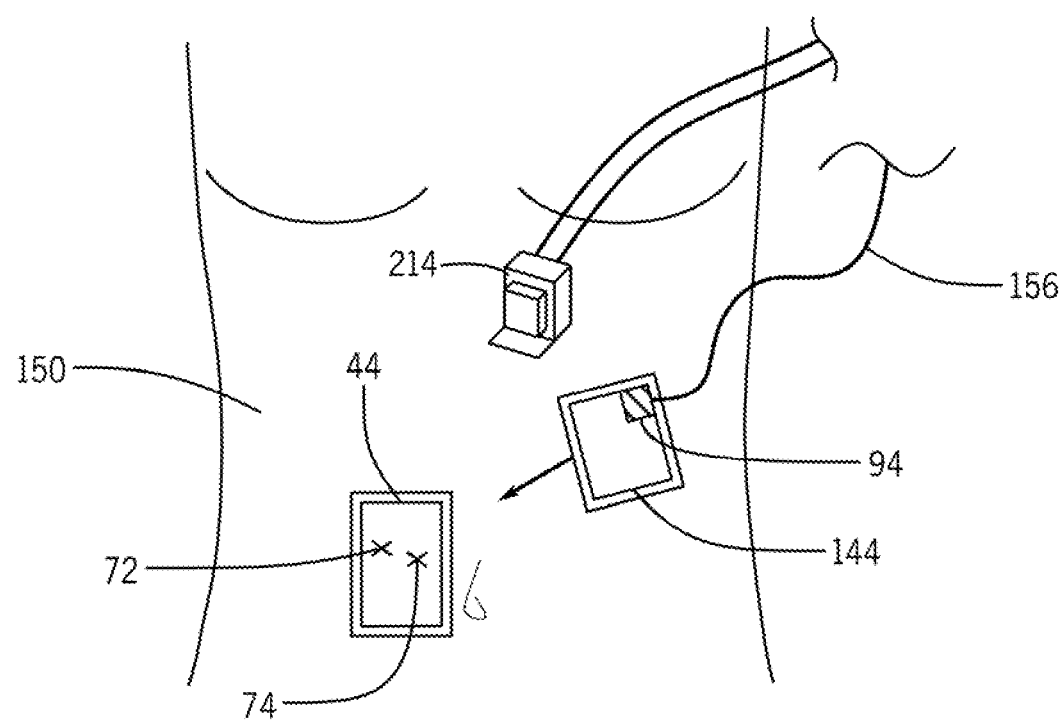
FIG. 11 is an exemplary body diagram that schematically illustrates the position of the surface frame during acquisition of a previous set of medical images with the realtime position of the surface frame or imaging probe with attached camera.
Figure 12:
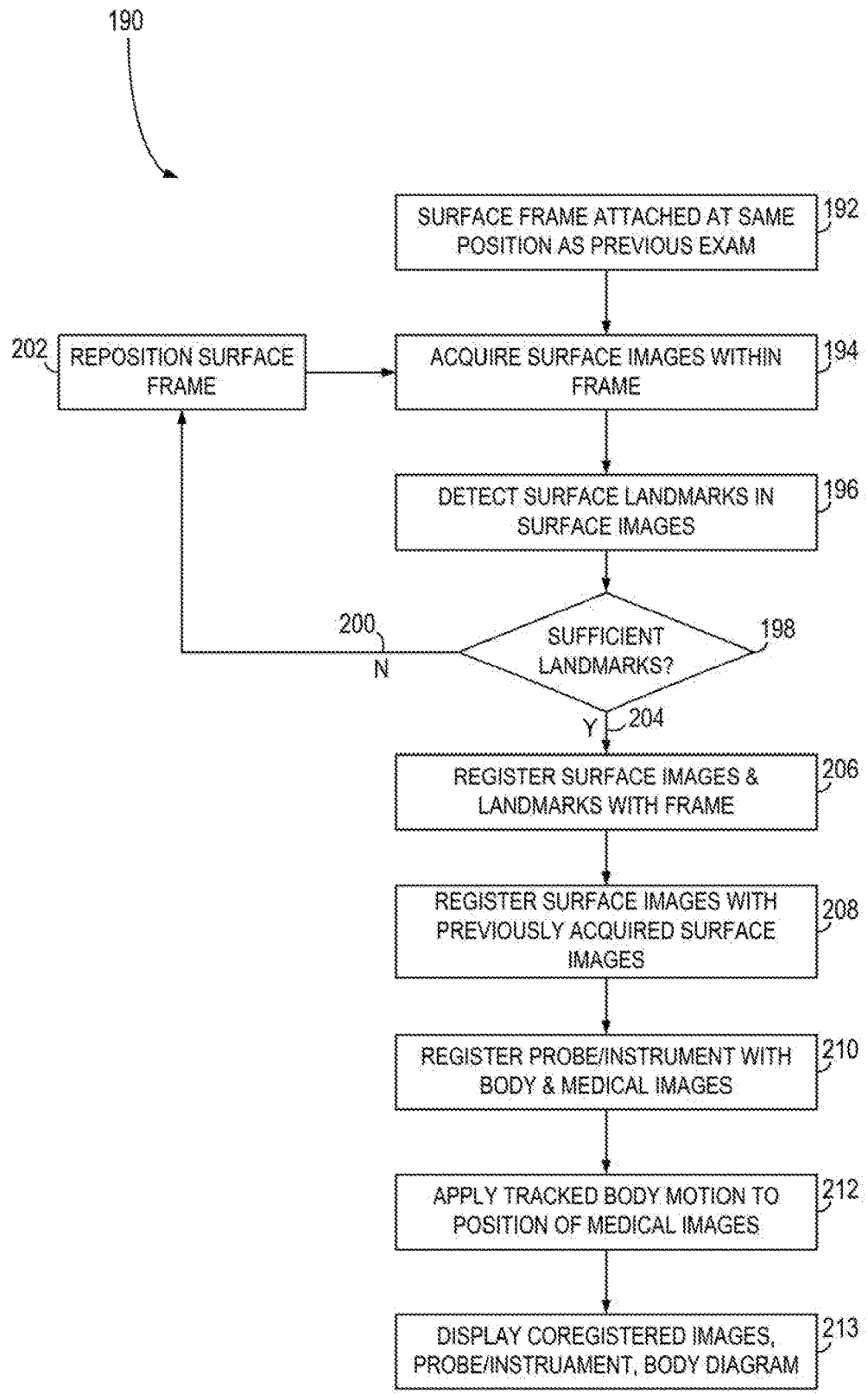
FIG. 12 is a flow chart illustrating the steps of a technique for registering an ultrasound probe or surgical instrument with set of medical images using detected surface landmarks, according to an embodiment of the invention.
Figure 13:
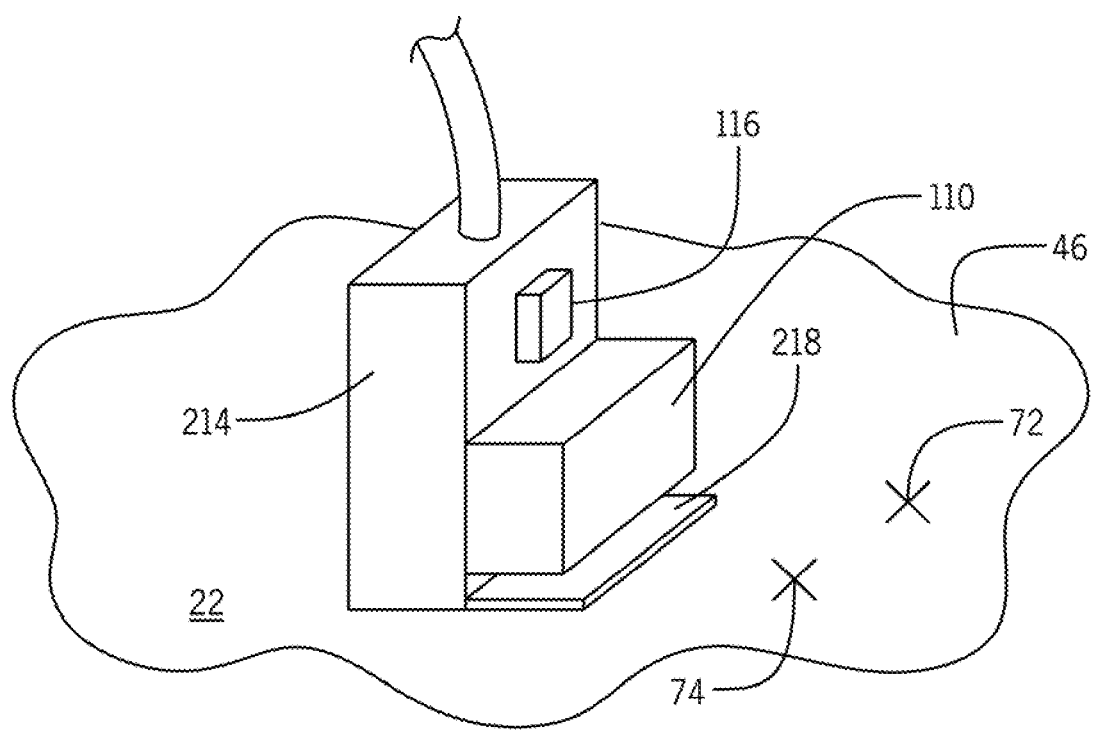
FIG. 13 is a schematic illustration of an ultrasound probe having a surface camera attached thereto, according to an embodiment of the invention.
Figure 14:
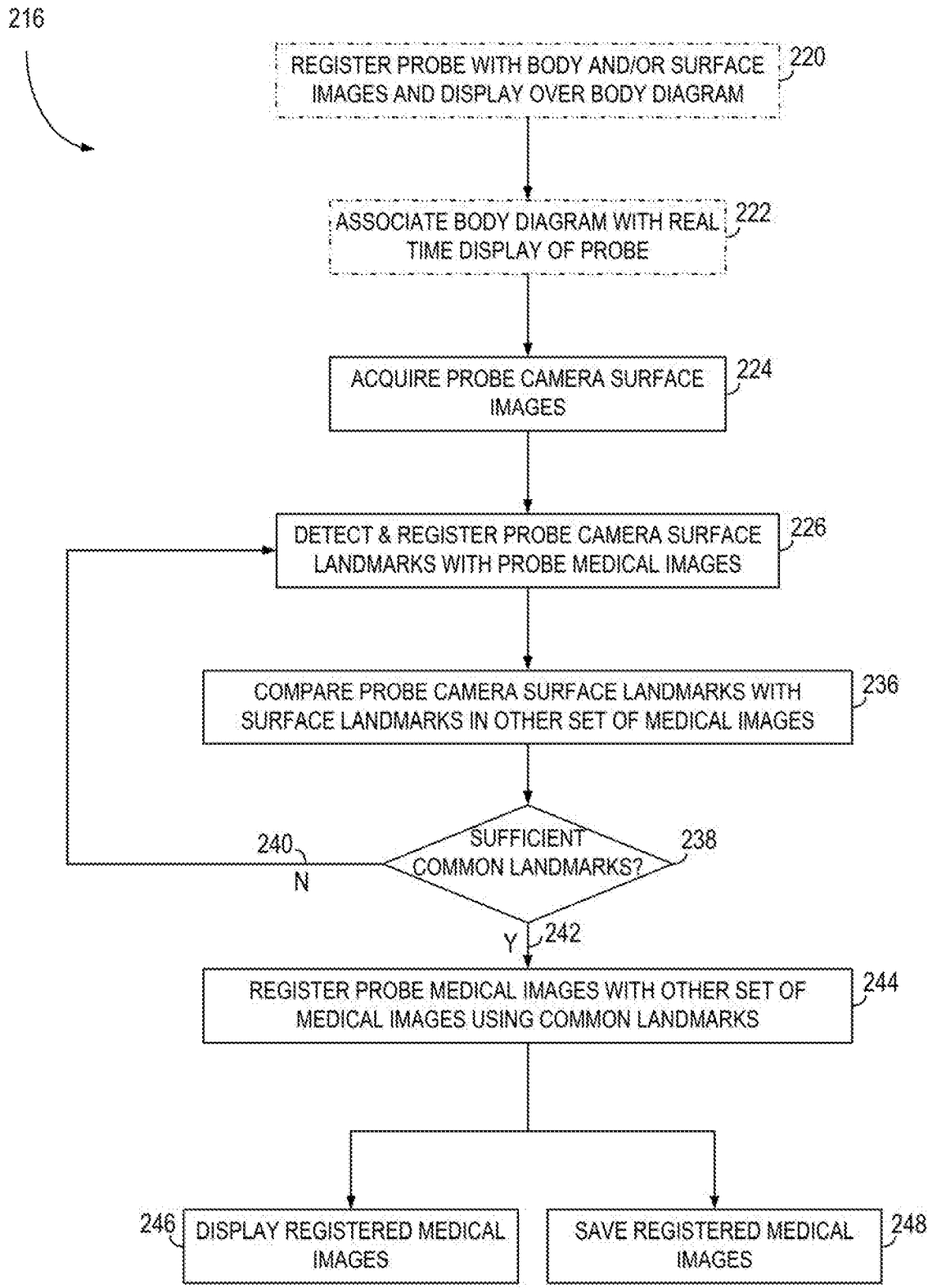
FIG. 14 is a flow chart illustrating the steps of a technique for registering a set of medical images acquired using an ultrasound probe with a set of medical images acquired using a different imaging modality based on detected common surface landmarks, according to an embodiment of the invention.

FIG. 9 illustrates the steps of a subroutine 148 usable with the technique 120 of FIG. 8 for positioning surface frame 144 in approximately the same location as surface frame 44 prior to acquisition of a second or subsequent set of medical images, according to an embodiment of the invention. Subroutine 148 operates in conjunction with the display of a body diagram 150 of the medical patient 22, which is illustrated in FIG. 11 and referred to in conjunction with the description of FIG. 9 as appropriate. Subroutine 148 begins when the body diagram 150 is registered with a first set of medical images obtained with the surface frame 44 included in the images. Since the position of surface frame 44 or landmarks 72, 74 are known in first set of images, they can be represented over the body diagram 150 as shown in FIG. 11. In an alternate embodiment, surface frame 44 is registered to the body of the medical patient 22 at step 154. The registration of the surface frame 44 to the body of the medical patient 22 is performed using one or more position sensors 94 attached to the surface frame 44 and using anatomical references. According to one embodiment, position sensors 94 may be wired sensors, such as magnetic sensors for example, that are coupled to image coregistration system 14 (FIG. 1) via a wired connection 156 and capable of being tracked in three dimensions. Alternatively, position sensors 94 may be wireless sensors such as optical or infrared markers that may be tracked using an optical tracking system or overhead infrared camera (not shown) that includes dedicated hardware and software for receiving reflected infrared light from the markers or emitted infrared light from small infrared light sources applied to the surface frame 44. The surface frame 44 is calibrated to the position sensors 94 using any known technique. Subsequently, the calibrated surface frame 44 is registered with the body of the medical patient 22 by matching the position of the surface frame 44 with known surface landmarks on the patient body and, optionally, aligning the surface frame 44 with the body axes or planes, for example coronal, sagittal, and/or axial planes. For example, a calibrated point on the surface frame 44 can be applied next to the umbilicus of the medical patient 22 and the surface frame 44 aligned with the sagittal plane of the body prior to attaching the surface frame 44 to the skin surface 46. After surface frame 44 is registered to the body, it can be fixed to the skin surface 46 (step 122 of technique 120) and its position relative to the body recorded with a corresponding set of medical images at step 158. Once the relative position of the surface frame 44 is determined with respect to the patient body, the body diagram 150 is generated and displayed together with the registered surface frame 44, as shown in FIG. 11.

Prior to acquisition of a set of medical images during a subsequent or second examination, the body diagram 150 is displayed to an operator to illustrate the position of the registered surface frame 44 or landmarks 72, 74 from the previous or first examination at step 160. Using position sensors 94 coupled to surface frame 144, the surface frame 144 is registered to the body of the medical patient 22 in a similar manner as described above. The position of the surface frame 144 relative to the body is then calculated and displayed in real time over the registered body diagram 150. Using the display, the operator is able to adjust the realtime position of surface frame 144 to match the approximate position of surface frame 44 from the previous set of images at step 162. Surface frame 144 is attached to the skin surface 46 at step 146.

Referring again to technique 120 of FIG. 8, after the surface frame 144 is attached to the skin surface 46 at step 146, a surface image within the surface frame 144 is acquired at step 164 and processed at step 166 to detect surface landmarks located on the skin surface beneath the surface frame. These surface landmarks are compared with surface landmarks identified in surface images acquired during the previous examination at step 168 to determine if sufficient common surface landmarks exist between the two surface images. If sufficient common landmarks are detected 170, medical images containing the surface frame 144 can be acquired and coregistered with the first set of medical images in the manner described below. If sufficient common landmarks are not detected sufficient landmarks not detected 172, the surface frame is repositioned on the body at step 174. The acquired second set of medical images is registered with the surface landmarks at step 176 in order to record the positional coordinates of the surface frame 144 relative to the body, in a similar manner as described above with respect to step 140.

Figure 10:
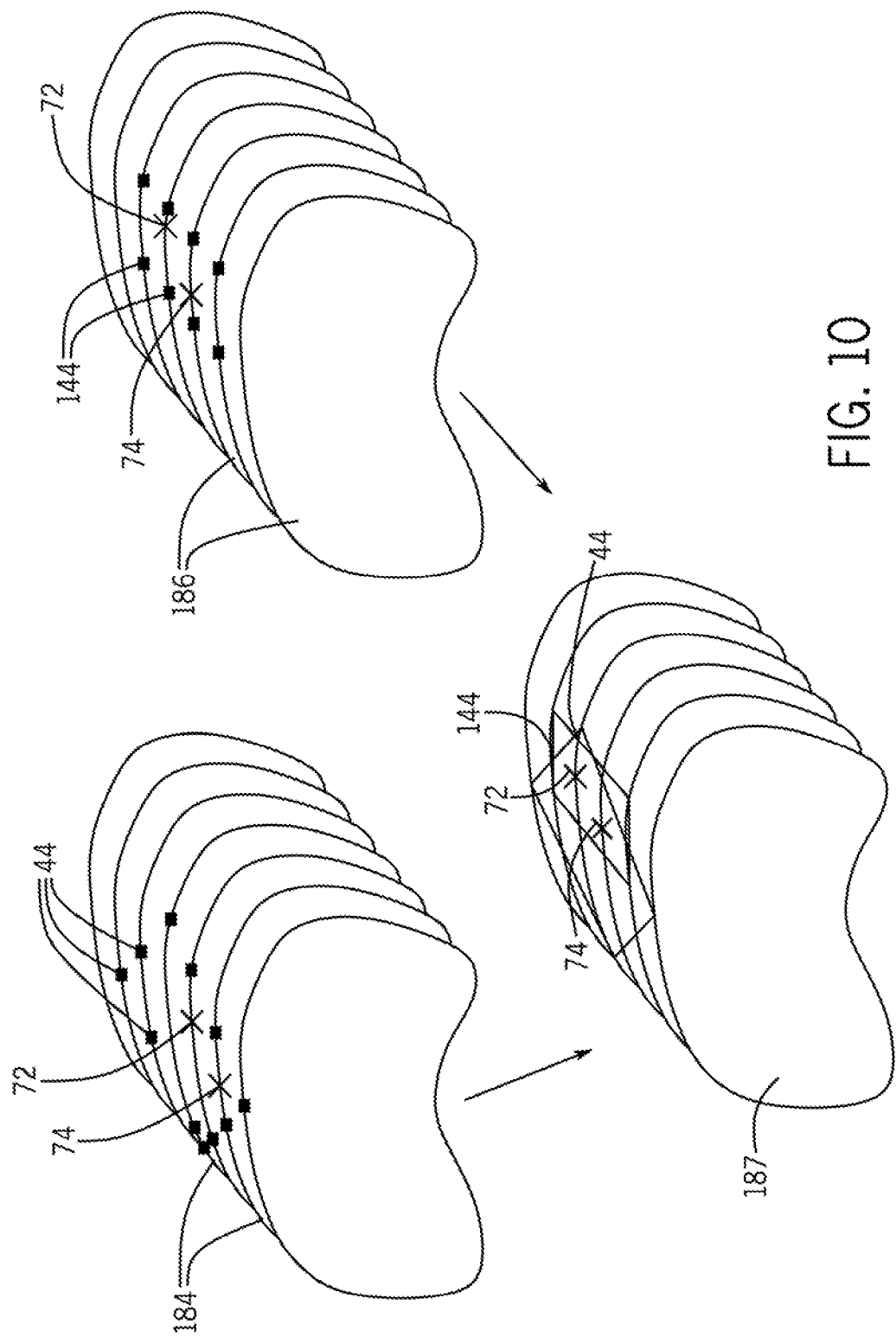
FIG. 10 illustrates exemplary medical images that include the surface frame of FIG. 2.

Once surface frame 144 is positioned at a location at which sufficient common landmarks are detected in the acquired surface image 170, a second set of medical images is acquired at step 178. The second set of medical images is registered with the surface landmarks 72, 74 at step 180 in a similar manner as described above for step 140. The first and second sets of medical images are then coregistered at step 182. The coregistration is carried out based on the detected position of the common surface landmarks 72, 74 in the first and second sets of medical images. Specifically, the position of the surface frame 144 relative to the body is determined based on the position of the surface frame 144 in second set of medical images. The surface images acquired within surface frame 144 are used to determine the position of the surface landmarks 72, 74 relative to the surface frame 144. The position of the surface landmarks 72, 74 in the second set of medical images is determined based on the registration between the surface image and the surface frame 144 and the location of the surface frame 144 within the second set of medical images. Subsequently, the position of surface landmarks 72, 74 can be displayed relative to the first set of medical images 184 and the second set of medical images 186, as shown in FIG. 10, and used to co-register the two sets of medical images 184, 186. The coregistered sets of medical images 187 can thereafter be displayed together at step 188, as shown in FIG. 10, and the determined positional coordinates of the common surface landmarks 72, 74 saved. Additional sets of medical images can be co-registered using the common surface landmarks 72, 74 in the manner described above.

In an alternative embodiment where surface frame 44 is used with a grid 84, the position of surface landmarks 72, 74 detected in the surface image can be localized within the surface frame 44 using grid 84. A fiducial marker (not shown), detectable in the later-acquired medical images, can be attached to the skin surface 46 at the location of each detected surface landmark 72, 74. If a transparent plate 90 is used with the grid 84, the transparent plate 90 can include multiple holes to allow the placement of fiducial markers while the surface frame 44 remains affixed to the skin surface 46. After the application of fiducial markers, the surface detector assembly 40 can be removed and the applied fiducial markers can be used for coregistration purposes, knowing their position in the respective medical images corresponds to the common surface landmarks detected in the surface images.

While the use of one surface frame is described above as being applied to the skin surface 46 prior to acquisition of surface images during each examination, multiple surface frames may be attached to the skin surface and used to identify surface landmarks and register the body position or a set of medical images with prior sets of medical images in an alternative embodiment. When more than one surface frame is used, the surface frames can be spaced and placed in different regions of the body, this way the body registration area is increased to allow increased registration accuracy. Regardless of whether one or multiple surface frames are utilized on the skin surface 46 during an examination, the accuracy in coregistering images acquired during different examination increases based on the number of surface landmarks that are detected. When three or more common surface landmarks are detected on the skin surface 46 between examinations, the positional coordinates of the common surface landmarks may be used to coregister the corresponding medical images without any separate reference to changes in the orientation of the body of the medical patient 22 between the examinations.

After the registration process between one or more sets of surface images and the body is completed by way of the location of the common surface landmarks, one or more previous sets of medical images are matched with the body. However, when the body moves, the co-registration between a prior set of images and the body is no longer valid and therefore needs to be repeated. This is particularly of interest when real time medical images registered with the body are obtained with hand held imaging probes, like ultrasound. The ultrasound images are registered with the body and other sets of images of the body. Also, when a medical instrument, for example a surgical implement such as a biopsy needle, is navigated to a target of known coordinates using medical images registered with the body, the body motion generates registration errors between the position of the surgical instrument and the body and the set of co-registered medical images. To address this limitation, an exemplary technique 190 is set forth with respect to FIG. 12 in which the positional shift of surface landmarks during an examination is calculated and applied to corresponding medical images to maintain the co-registration between a previous set of medical images and either real time medical images or the real time position of an ultrasound probe or medical instrument within an acceptable range. The techniques set forth herein may be carried out to maintain such co-registration within a range of a few millimeters.

Technique 190 begins at step 192 with surface frame 144 attached at approximately the same position on the skin surface 46 as surface frame 44 was attached during a previous examination. Surface images within surface frame 144 are acquired at step 194 and surface landmarks are detected within the acquired surface images at step 196, in a similar manner as described above with respect to steps 124, 126 of technique 120. Technique 190 determines whether sufficient landmarks have been detected within the acquired surface images at step 198. If sufficient landmarks are not detected 200, surface frame 144 is repositioned at step 202. If sufficient landmarks are detected 204, the acquired surface images are registered with the landmarks and the surface frame 144 at step 206.

At step 208, the surface images acquired using surface frame 144 are registered with surface images acquired using surface frame 44 during the previous examination. At step 210 the ultrasound imaging probe or medical instrument is registered with the surface frame 144 by aligning the probe or medical instrument with the surface frame 144 in a predetermined position. According to various embodiments, this alignment may be carried out by selecting targets contained in the surface frame 144 or by matching the position and orientation of the ultrasound probe or medical instrument with the position and orientation of the surface frame 144. It is contemplated that alternative methods may be used to register the ultrasound probe or medical instrument with surface frame 144. When several surface detector frames are attached to a body, the imaging probe or medical instrument can be registered with the multiple surface frames and corresponding surface common landmarks to increase the accuracy of the registration between the imaging probe or medical instrument and the body.

After the registration steps described above, in some embodiments of the invention the surface landmarks are identified and marked with sensors or markers for future positional tracking and the surface frame 144 can be removed. Removing the surface frame 144 would allow the movement of the handheld probe over the body surface of interest, without interference from the surface frame 144.

Patient body motion is tracked at step 212 by tracking motion of the surface landmarks on the body based on positional changes in the surface frame 44 as detected using position sensors 94. Surface frame 144 is attached to the skin surface 46 of the medical patient 22 and position sensors 94 are attached to the surface frame 144. When the body of the medical patient 22 moves, the surface frame 144 moves with the body and the displacement is tracked by position sensors 94. Coordinates of the detected surface landmarks within surface frame 144 are calculated with respect to the body of the medical patient 22, since the surface landmarks are registered with the surface frame 144 and the position of the surface frame 144 is known relative to the world coordinate system of the medical imaging device 12 via position sensors 94. Registration with the medical images acquired during the previous examination is continuously or dynamically adjusted based on the tracked body movement by applying the position or displacement data of the surface landmarks 72 as determined by position sensors 94 to the registration data with the previously acquired set of medical images. In embodiments where the surface frame 144 is removed after registration, body motion may be tracked by monitoring positional changes in the sensors, fiducials, or markers applied to the skin surface after removing surface frame 144.

When the imaging probe or medical instrument, surface frame 144 and a previous set of images are registered to the body, the real time position representation of the probe with its image or the surgical instrument representation can be combined with the previous set of medical images or a body diagram and displayed together at step 213. The display of coregistered data can be used to show fused images of a prior images set with real time imaging probe images and guide the use of a medical instrument to an internal target, such as, for example a cyst or tumor within the body of the medical patient 22.

In addition to surface handheld ultrasound probes, endocavitary probes can be registered as described above and their images co-registered with the body and prior sets of medical images. The endocavitary or ultrasound imaging probes can be handheld, robotically guided, or capable of freely moving over or inside the body such as, for example, an ingested capsule which records video sequences throughout the digestive tract. As long as the imaging probe is registered to the body and the position of the imaging probe is tracked, images acquired using the imaging probe may be co-registered with previously acquired medical images based on detected body movement and the acquired surface images in the manner set forth above.

The handheld probe or robotic probe image registration with the body or body images described above is not limited to single frame images but also can include multiple frames, like sequential frames in video clips or 3D images obtained with the probes. Each frame in a sequence of frames is registered as above and the registered pixels in the frames can be used as reference to register the voxels in the reconstructed 3D images. Alternatively, in a calibrated three-dimensional ultrasound probe, the voxels are directly registered to the body and prior body images.

Referring now to FIGS. 13-16 together as appropriate, an alternative embodiment is set forth that utilizes a surface camera 110 coupled to a handheld imaging probe 214 to track the position of the handheld imaging probe 214 and calibrate acquired medical images to the tracked position of the handheld imaging probe 214. The medical images are then coregistered with medical images acquired during a previous or subsequent examination using the technique 216 set forth in FIG. 14. An optional transparent plate 218 (shown in phantom) may be coupled to the handheld imaging probe 214 to flatten the skin surface 46 as the handheld imaging probe 214 passes over the skin surface 46.

Technique 216 employs a hand held or automated positionally tracked imaging probe 214 with an attached surface camera 110, where the surface image is spatially calibrated to the imaging probe 214. Technique 216 begins at optional step 220 (shown in phantom) by registering the handheld imaging probe 214 with the body of the medical patient 22. This step can be done by aligning the imaging probe 214 with the body axes of the medical patient 22 and a body landmark of the medical patient 22, like the umbilicus, or multiple body landmarks. If at the beginning of an examination, this step may also include a calibration between the medical image acquired using imaging probe 214 and the surface image acquired using attached surface camera 110. After this optional step, a second optional step 222 associates a body diagram 150 (FIG. 11) of the medical patient 22 with the real time display of the position of the imaging probe 214 over the body diagram 150. The body diagram 150 may also include a display the position of surface landmarks 72, 74 and the position of surface frame 44 from a first set of images obtained with surface frame 44, relative to the body, as described for the positioning of surface frame 144 above and as seen in FIG. 11. The optional steps can guide the operator of the imaging probe 214 to the body surface region with the common surface landmarks 72, 74 detected with the first set of images. The surface camera 110 acquires surface images of the skin surface 46 at step 224 as the handheld imaging probe 214 is moved over a region of interest on the body of the medical patient 22. Surface images acquired using surface camera 110 are processed within the probe surface image module 112 of processor 36 and surface landmarks located on the skin surface 46 are detected and saved at step 226. As described above, these surface landmarks may represent a skin texture pattern or microfeatures at the skin surface 46, skin marks such as moles, surface vessels, or any other detectable landmarks. The surface image(s) obtained with the surface camera 110 are calibrated to the handheld imaging probe 214 and the medical images acquired using handheld imaging probe 214. Therefore, the position of each surface landmark detected in the surface image(s) is registered relative to the handheld imaging probe 214 and the medical images generated by the positionally tracked imaging probe 214 with the known position and orientation.

Figure 15:
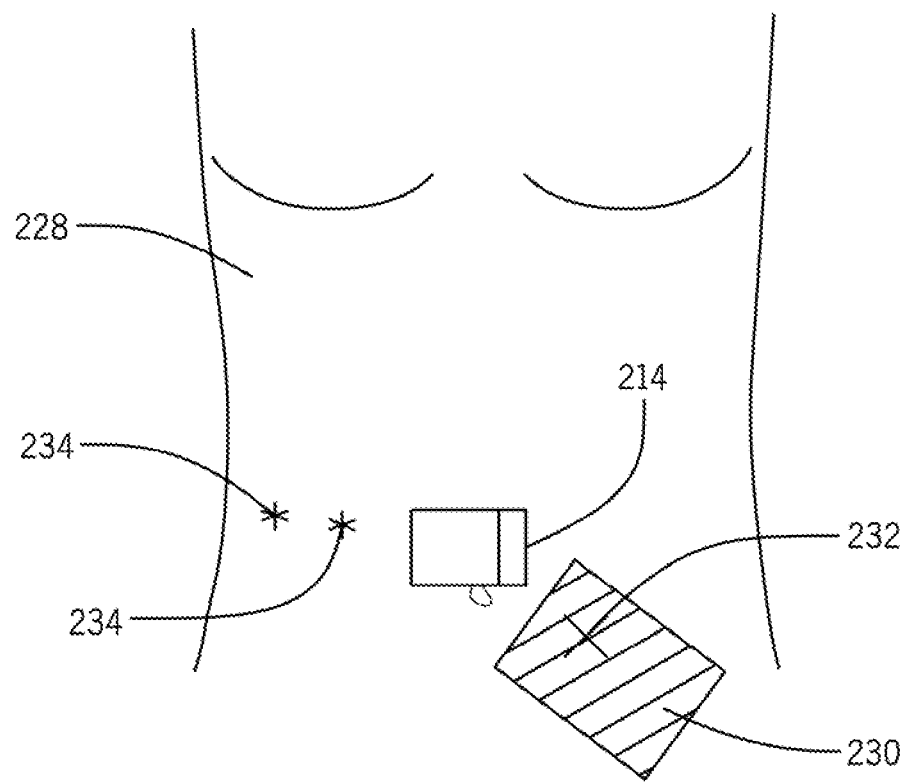
FIG. 15 is an exemplary body diagram that schematically illustrates the position of the handheld imaging probe of FIG. 13 relative to surface images corresponding surface landmarks acquired using the surface camera attached to the handheld imaging probe and surface landmarks detected during previous examination.

Registration of the handheld imaging probe 214 with the body diagram can be done separately from the surface landmark detection or can be done during the detection surface landmarks as the surface landmarks are matched with a previous body diagram with known surface landmarks and prior medical images. Because the handheld imaging probe 214 is registered with the body and includes position sensors that can be used to monitor the realtime position of the handheld imaging probe 214 relative to the body of the medical patient 22, a body diagram 228 as shown in FIG. 15 can be generated to display the realtime position and orientation of the handheld imaging probe 214 along with a cumulative map 230 of surface images acquired using surface camera 110 along with the position of any surface landmarks 232 identified within those surface images. Positional information displayed within body diagram 228 can then be stored. The relative position of surface landmarks 234 detected during a previous examination may also be displayed on the same body diagram 228 to aid in guiding the handheld imaging probe 214 to detect common surface landmarks.

At step 236 the surface landmarks detected with the surface camera 110 attached to handheld imaging probe 214 are compared with the surface landmarks obtained from surface images acquired during a previous examination, using either surface detector assembly 40 with associated surface frame 44 or with surface camera 110 attached to handheld imaging probe 214. Technique 216 determines whether common surface landmarks exist between the surface images at step 238. If common surface landmarks do not exist in the surface images 240, technique 216 may return to step 226 to compare other surface images from the current and previous examination. If common surface landmarks are detected between the surface images 242, technique 216 proceeds to coregister medical images acquired using handheld imaging probe 214 with the previously acquired set of medical images by matching the position of the common surface landmarks at step 244. The coregistered medical images are displayed at step 246 and saved at step 248.

When the position of sufficient common surface landmarks, for example at least three landmarks, is obtained, the imaging probe 214 can be registered with the previous set of images. The surface deformation during scanning may degrade the registration accuracy, therefore it would be preferable for the imaging probe 214 to cause minimal surface deformation during the acquisition of the surface landmarks for the registration with a prior set of images. After the registration process is completed, the surface deformation is expected to cause less interference with the registration since the internal structures are less likely to be displaced by the surface deformation caused by the imaging probe 214.

Aspects of the techniques disclosed above may be extended to the imaging of deformable body parts, such as the breast, to aid in the coregistration of different sets of medical images. An exemplary technique 250 for co-registering sets of medical images of the breast is set forth in FIG. 16. As described below, technique 250 detects multiple common surface landmarks between sets of medical images thereby permitting medical images of the deformable body part to be co-registered with one another with greater accuracy than can be accomplished using prior art techniques.

Figure 16:
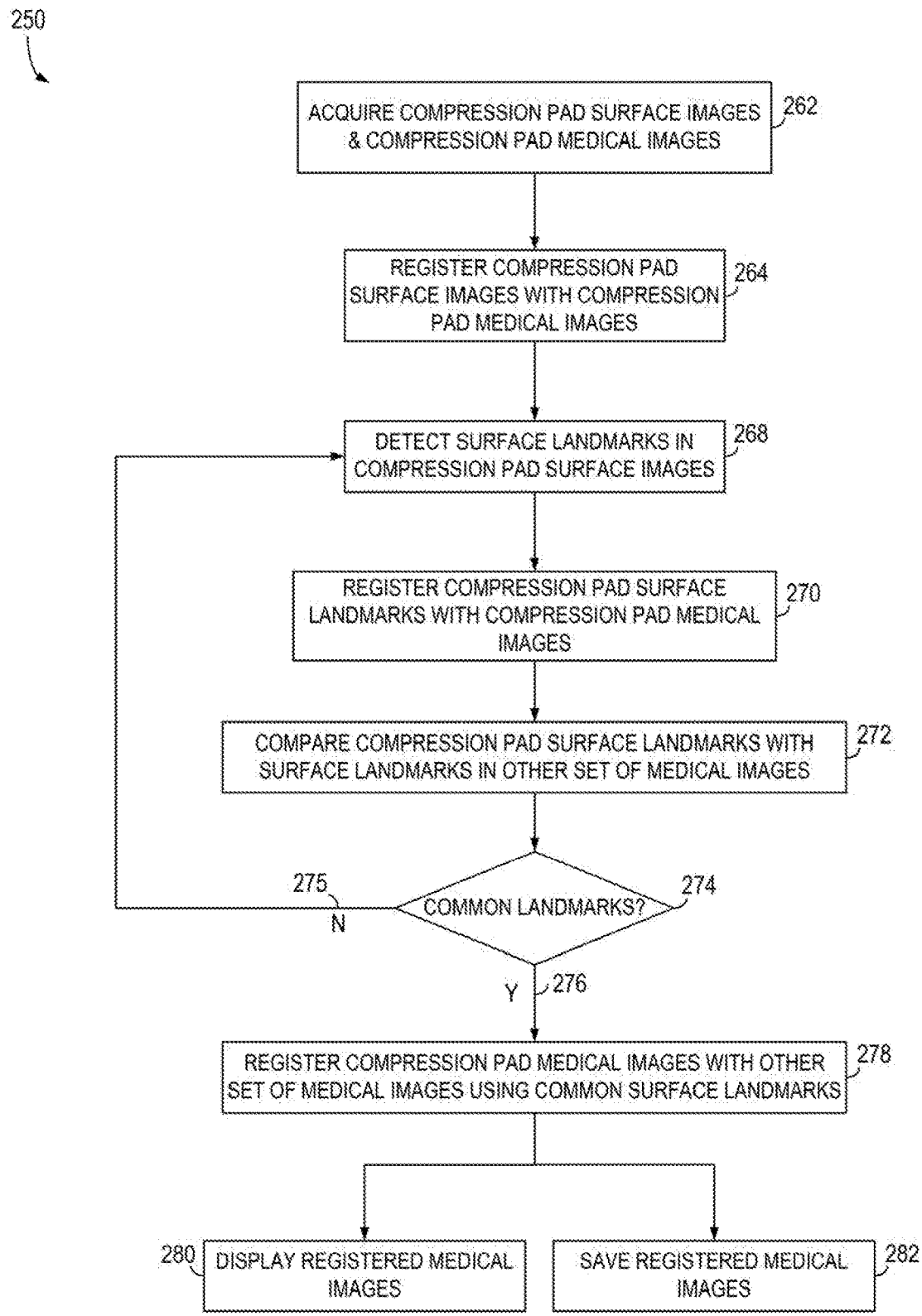
FIG. 16 is a flow chart illustrating the steps of a technique for registering a set of medical images acquired using a compression pad with a set of medical images acquired using a different imaging modality based on detected surface landmarks, according to an embodiment of the invention.

Referring now to FIGS. 16 and 17 together as appropriate, technique 250 is carried out using a pair of compression pads 252, 254 that are applied to the opposing surfaces of the deformable body part 256. The compressed surface of the deformable body part 256 exposes an area of skin which is in contact with the compression pads 252, 254. The compressed skin under compression pads 252, 254 is analyzed using surface images acquired by a respective surface camera 258, 260 coupled to compression pads 252, 254 for surface landmarks. Surface cameras 258, 260 are constructed in a similar manner as camera system 48 of FIG. 2. In one embodiment, surface cameras 258, 260 and corresponding compression pads 252, 254 are integrated in a common structure. In such an embodiment, surface cameras 258, 260 each include a matrix of detectors with an optical part or lens, similar to lens 56 of FIG. 2, to form a surface image. Alternatively, surface cameras 258, 260 are provided as standalone devices that are detachable from compression pads 252, 254. In embodiments where compression pads 252, 254 are constructed with a grid similar to grid 84 of surface frame 44 (FIG. 6), surface landmarks may be marked at the skin surface with a fiducial marker applied to the skin surface.

During step 262 of technique 250, surface images of the skin surface of the deformable body part 256 are acquired using surface cameras 258, 260. At step 262, either two-dimensional or three-dimensional tomosynthesis images of the deformable body part 256 are acquired with the deformable body part 256 positioned between the compression pads 252, 254. Because the compression pads 252, 254 are constructed to be transparent to light in order to obtain surface images using surface cameras 258, 260, the cameras 258, 260 are removed prior to acquisition of the medical images to prevent interference with the medical images. In an alternative embodiment, the surface images may be acquired after acquiring the medical images. In embodiments that acquire mammography or tomosynthesis images, the medical images are acquired using an x-ray tube 261 (shown in phantom) that emits a beam of x-rays 263 (shown in phantom) toward a detector assembly 265 (shown in phantom). These acquired medical images may demonstrate abnormal findings such as, for example, small nodules, calcifications, focal densities, and the like, which are reviewed with another examination after a period of time, such as six or twelve months to assess for changes, which can guide the medical management of such findings.

The surface images acquired using surface cameras 258, 260 are registered with the medical images acquired using compression pads 252, 254 and the body or body part of the medical patient 22 at step 264. In one embodiment, the compression pads 252, 254 may contain one or more optional markers 266 (shown in phantom), which can be detected in the medical images and the surface images and can be used to register the surface images with the medical images.

At step 268, the acquired surface images are analyzed to detect surface landmarks on the skin surface of the deformable body part 256, including, for example, a skin texture pattern, micro features, skin marks including moles, surface vessels or any other detectable landmarks. The detection of the surface landmarks can be performed with optical, near infrared or infrared light and in combination with the use of surface cameras 258, 260, in a similar manner as described with the system of FIG. 2.

Since the surface images are registered with the body part as above, the detected surface landmarks can be registered with the body part and recorded in the corresponding medical images at step 270. The surface landmarks and image position can be saved with the set of medical images. The detected surface landmarks can then be compared with surface landmarks associated with medical images acquired during previous examinations at step 272. Based on the comparison, technique 250 determines whether common surface landmarks exist in the medical images acquired using compression pads 252, 254 and the previously acquired medical images at step 274. If common landmarks are not detected in the surface images from the two examinations 275, technique 250 returns to step 268 and either reattempts to detect surface landmarks in the surface images acquired using the compression pads or repositions the compression pads. If common landmarks are detected in the surface images from the two examinations 276, technique 250 proceeds to coregister the medical images acquired using compression pads 252, 254 with the previously acquired set of medical images by matching the position of the common surface landmarks at step 278. The coregistered medical images are displayed at step 280 and saved at step 282.

In one embodiment, when the position of a surface landmark at the breast skin surface is known from a previous examination, the surface landmark can be detected and marked with a fiducial marker before the breast is positioned between the compression pads 252, 254 for a medical image. The surface landmark position can be obtained using a surface frame 44 and associated grid 84 similar to that described in FIGS. 2-6, which can be removed after the surface fiducial, detectable in medical images is applied on the skin surface 46 at the position of the surface landmark. With skin fiducials applied at skin surface 46, the direction and magnitude of skin and tissue displacement can be visualized in the obtained medical images. When multiple skin fiducials are applied, the shape of the applied fiducials can be different to aid identifying the fiducials corresponding to different surface landmarks.

In the case of a mammogram, a small abnormal finding can appear at different locations in temporally different mammographic images of same breast, taken under same technical conditions, due to differences in breast positioning and deformation between the compression pads 252, 254. The abnormal findings and breast tissue in the region will be displaced in the direction of the relative movement of skin in the proximity of the abnormal finding as shown in FIGS. 18A-D. The positional correlation of abnormal findings between image sets or the coregistration of different images is important for the medical interpretation.

In the cranio caudal projection (CC) mammographic image taken at time T0 (FIG. 18A), target A in the breast is located close to the superior breast skin surface 284, laterally, and target B in the breast is located close to the inferior breast skin surface 286, medially. In a CC mammographic image taken at a different time T1 (FIG. 18B) the breast is rolled medially and target A appears displaced in the medial direction, while target B appears displaced in the lateral direction. The direction of a target displacement follows the direction of displacement of the skin in closest proximity. A target closer to the skin surface, will follow the skin direction and magnitude of displacement closer than a target deeper in the breast, which will follow the direction of displacement at a smaller magnitude than the target closer to skin. For a target at equal distance between the compression pads 252, 254 and breast surface skin, there may be no displacement of the target between two temporally different images.

Figure 18B:
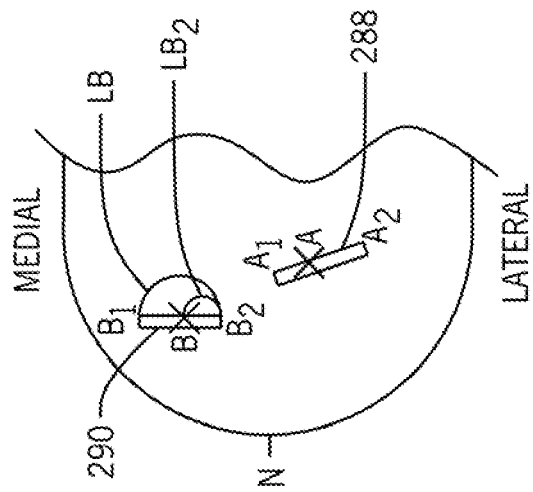
FIG. 18 includes schematic medical and diagrams of a breast illustrating the displacement of two targets between images acquired at different times.
Figure 18D:
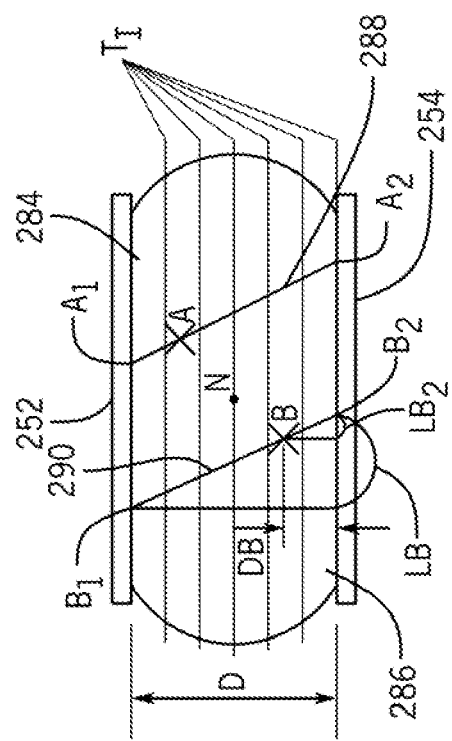
Figure 18A:
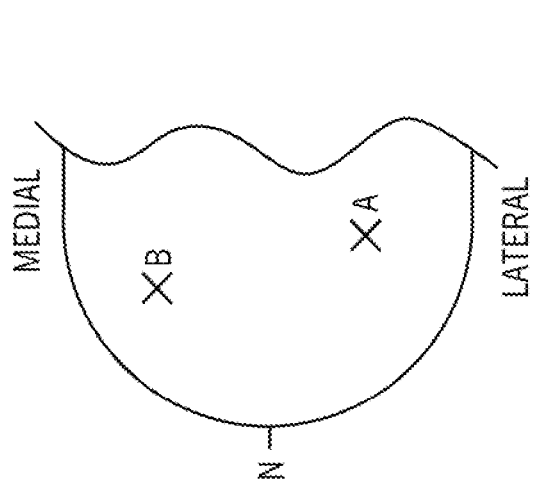
Figure 18C:
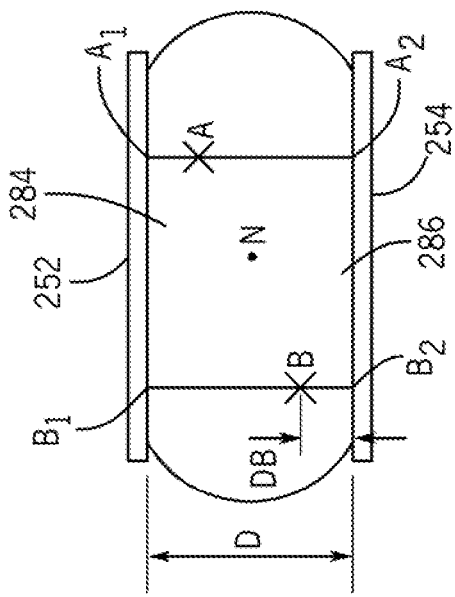

FIGS. 18C and 18D are body diagrams representing the relative position of targets A and B relative to compression pads 252, 254 and the relative displacement of targets between time T0 and time T1 respectively. One or more of the body diagrams may be displayed to a clinician as part of a graphical user interface embodied on the display 28 of image coregistration system 14 to aid the clinician in detecting targets A and B during a follow-up examination as explained in additional detail below. In the image taken at time T0, a line perpendicular on the compression pads 252, 254 and through a target, A or B for example, or a line that connects a target in the breast and closest surface point at both compression pads 252, 254 can be generated. As shown in FIG. 18D, for example, the points where lines 288, 290 intersect the skin surface can be identified, A1 and A2 for target A and B1 and B2 for target B. For the 2D images, it will be the same point corresponding to the target in the mammogram, A or B and projected in the skin surface images. For the three-dimensional images, a line through a target can connect with the closest skin point at the compression pads 252, 254. The surface landmark in closest proximity to the skin points determined above can be identified and recorded in the skin surface images, associated with the corresponding mammographic views.

With a second mammographic image taken at time T1, the previously determined skin surface features corresponding to a target, A1, A2 and B1, B2, are detected in the skin surface images registered with the mammogram image taken at time T1. A line 288 connecting A1 and A2 or a line 290 connecting B1 and B2 can be generated and target A or B are expected to be found along or in the proximity of the line, 288 or 290. In alternative embodiments, lines 288 or 290 may be replaced by an area where targets A or B are expected to be found in the image taken at time T1, such as, for example, highlighted oval or circular regions extending between points A1, A2 and B1, B2, respectively, which may guide a clinician to the expected location of targets A or B during a follow-up examination. If the mammographic image taken at time T1 is composed of a set of 3D images, parallel to each other, like tomosynthesis images, line 288 will connect the surface landmark points at the skin compressed by the compression pads 252, 254 and intersect each three-dimensional slice, TI. Furthermore, the depth of a target A or B in the image taken at time T1 can be calculated, once the target A or B is identified in the image. For example, the depth of target B from the inferior breast skin surface 286 is DB=(LB2×D)/LB. The calculated line or region where a target seen in the image taken at time T0 is expected in the image taken at time T1 can be marked in the mammographic image to aid finding the target A or B. While one surface landmark is described above at each skin surface 284, 286 to locate corresponding targets A and B, more than one surface landmark can be detected in the proximity of a given target A, B and an averaged position used for positional calculations.

In the tomosynthesis or MRI images of the breast, the depth of a target in a first set of medical images is known, since the medical images are three dimensional. The depth information can be used to further narrow the region where the same target is expected in the second set of breast images. For example in FIG. 18C, if depth DB is known for target B, the region where the target is expected in the second set of images, FIG. 18D is LB2, smaller than LB where the depth is unknown. The region where target B is expected can be calculated using the formula LB2=(DB×LB)/D. When the depth of a target is known from the three-dimensional images obtained at time T0, one surface image, for example taken at the pad closer to target, can be used to determine the expected position or range where the target can be found in the image taken at time T1.

Figure 19:
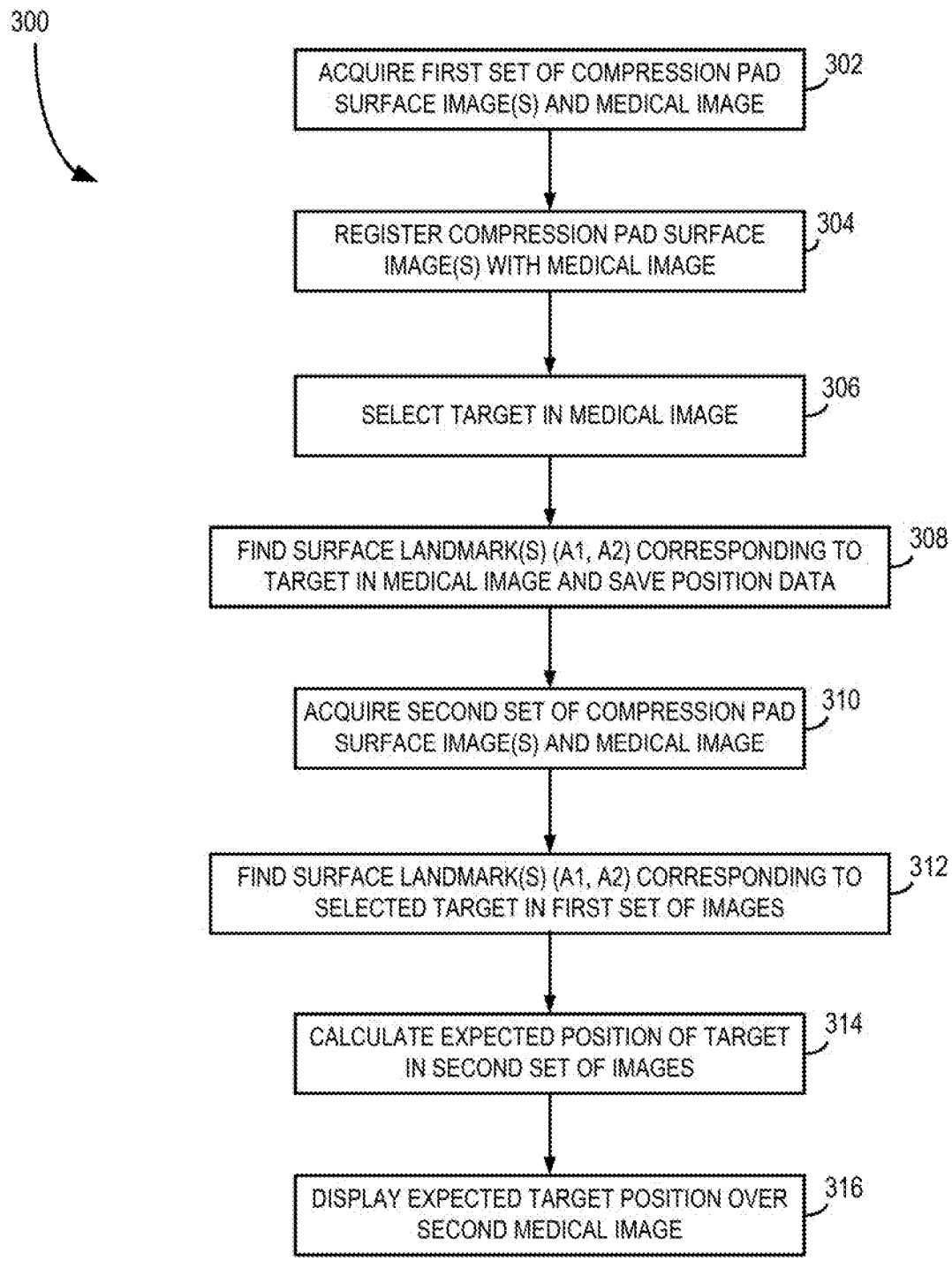
FIG. 19 is a flow chart illustrating the steps of a technique for obtaining the expected position of a target within a medical image, according to an embodiment of the invention.

The steps of a technique 300 to obtain the expected position of a target in the breast of a medical patient 22 are shown in FIG. 19, according to an embodiment of the invention. The technique 300 begins at step 302 by acquiring a first set of images at time T0, including one or more skin surface images acquired using compression pads 252, 254 and one or more medical images of the breast. The compression pad surface image(s) is registered with the medical image(s) at step 304 in the manner described above. The operator or clinician selects a target, A, in the medical image at step 306 via a graphical user interface such as one presented on display 28 (FIG. 1). One or more surface landmarks, A1, A2, are located corresponding to target A in the medical image and corresponding positional data is saved at step 308. A second set of images is acquired at time T1 during a subsequent examination at step 310. This second set of images includes one or more surface images acquired using compression pads 252, 254 and one or more medical images. One or more surface landmarks A1, A2 are located within the acquired medical images that correspond to the selected target A from the first set of images at step 312. The expected position of target A in the second set of images is calculated at step 314 and the expected position of target A is displayed as an overlay over the medical image(s) acquired during the subsequent examination at step 316.

The above methods of predicting the position of a target in a second set of breast images can be applied to same type of images or modality or across modalities when images of the breast are obtained with compression pads. Modalities that require the breast positioned with at least one pad include mammography, three-dimensional mammography or digital breast tomosynthesis (DBT), MRI, breast specific gamma imaging (BSGI) or positron emission mammography (PEM).

In one embodiment, one surface image only is obtained with one of the compression pads 252, 254 in both first and second examinations. At least one common surface landmark in the proximity of a target A, B is used to calculate the projected position of a target A, B in a second medical image or set of medical images, when the position of a target A, B in the first medical image or set of medical images is known. The nipple, N, can be used as a reference landmark to position the breast between the compression pads 252, 254 in same position with different examinations, to minimize the translation misalignment. The position of at least a common surface landmark is determined in the first and second medical image or set of medical images and the direction and magnitude of the displacement of the surface landmark can be calculated. The tracked target A, B in the breast, detected in the first medical image or set of medical images will move to a different location in the second medical image or set of medical images, following the direction of the displacement of the surface landmark in the second image or set of images when the target A, B is closer to the compression pads 252, 254 with the surface image. The target A, B will move in the opposite direction to the surface landmark displacement when closer to the other compression pad 254, 252.

The technique described above for determining the expected position of a target A, B in a breast medical image taken at a different time with the breast compressed between two compression pads 252, 254 can be extended in a similar manner to medical images taken in medio lateral (ML), medio lateral oblique (MLO) orientation for mammographic images or ML compression in prone position with the three-dimensional MRI images.

In an alternative embodiment, the displacement of surface landmarks between images T0 and T1 can be measured and used to reposition the breast closer to the position it had with the T0 image, to aid in the comparison and coregistration of medical images. The repositioning of the breast can be performed manually or can be automated as described with prior art (reference).

The set of medical images with associated surface landmarks obtained with compression pads 252, 254 can be compared with a different set of medical images with common surface landmarks obtained with a surface frame 44 or handheld imaging probe 214 with attached surface camera 110, or a different set of medical images obtained with compression pads 252, 254. The surface images are compared among different sets of medical images and when common surface landmarks are found, the different sets of images can be registered together, as described with respect to FIG. 16. The registered images can be displayed and saved.

A technical contribution for the disclosed method and apparatus is that it provides for a computer implemented technique for coregistering medical images or aid the correlation of different medical images for interpretation purposes. The technique determines the coregistration based on the position of surface landmarks positioned on or directly beneath the skin surface, which are detected using surface images. The technique determines the location of surface landmarks using a surface detector assembly that includes a surface frame coupled to the skin surface of a medical patient and a camera coupled to and registered with the surface frame. One or more medical images is also acquired while the surface frame is coupled to the skin surface of the patient and the positional coordinates are determined relative to the medical images based on the position of the surface frame in the medical images. A similar procedure is carried out during a subsequent examination to determine position coordinates of surface landmarks relative to a second set of medical images. The sets of medical images are coregistered based on positional coordinates of common landmarks detected in surface images acquired during the two examinations.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, a system for coregistering medical images includes a surface detector assembly positionable on a skin surface of a medical patient. The surface detector assembly includes a surface frame and a camera system coupled to the surface frame and configured to acquire surface images of a portion of the skin surface of the medical patient positioned proximate a lower surface of the surface frame. The system also includes a processor having a surface frame image module connected to a signal output of the camera system and programmed to identify positional coordinates of at least one common surface landmark within the acquired surface images. The processor also includes a coregistration module programmed to co-register a first medical image of the medical patient with a second medical image of the medical patient based on the positional coordinates of the at least one common surface landmark identified by the surface frame image module, positional coordinates of the surface frame within the first medical image, and positional coordinates of the surface frame within the second medical image. A display module generates a display of the at least one common surface landmark relative to the surface frame on a body diagram of the medical patient.

According to another embodiment of the invention, a method of coregistering medical images includes acquiring a first surface image of a first skin surface of a medical patient using a surface detector assembly comprising a surface frame coupleable to the skin surface and a camera system registered to the surface frame. The method also includes determining positional coordinates of at least one surface landmark in the first surface image, acquiring a first medical image of the medical patient having the surface frame depicted therein, and acquiring a second surface image of a second skin surface of the medical patient, the second skin surface at least partially overlapping the first skin surface. The method further includes determining positional coordinates of at least one surface landmark in the second surface image, comparing the at least one surface landmark in the first surface image to the at least one surface landmark in the second surface image, identifying at least one common surface landmark based on the comparison, and coregistering the first medical image with the second medical image based on positional coordinates of the at least one common surface landmark.

According to yet another embodiment of the invention, a non-transitory computer readable storage medium has stored thereon instructions that cause a processor to access a first medical image of a medical patient having a first surface frame depicted at a first position on the medical patient, access a first surface image acquired of a skin surface of a medical patient beneath the first surface frame, and detect surface landmarks within the first surface image. The instructions further cause the processor to access a second medical image of the medical patient having a second surface frame depicted at a second position on the medical patient, the second position at least partially overlapping the first position, access a second surface image acquired of a skin surface of a medical patient beneath the second surface frame, and detect surface landmarks within the second surface image. The instructions further cause the processor to compare the surface landmarks within the first surface image to the surface landmarks within the second surface image, identify at least one common surface landmark within the first surface image and the second surface image based on the comparison, and coregister the first medical image with the second medical image based on positional coordinates of the at least one common surface landmark.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for registering medical images comprising:
   a surface detector assembly positionable on a skin surface of a medical patient, the surface detector assembly comprising:
   a surface frame comprising a lower surface configured to attach to the skin surface, wherein the surface frame provides a frame of reference for the surface detector assembly to detect skin surface landmarks by bounding a portion of the skin surface;
   a camera system coupled to the surface frame, such that the camera system is fixedly positioned with respect to the surface frame, wherein the camera system is configured to acquire surface images of the portion of the skin surface of the medical patient located within boundaries of the lower surface of the surface frame; and
   a processor comprising:
   a surface frame image module connected to a signal output of the camera system and programmed to analyze the acquired surface images and detect the surface landmarks on the skin surface and determine relative positional coordinates of at least one common surface landmark with respect to the surface frame; and
   a coregistration module programmed to co-register a first medical image of the medical patient with a second medical image of the medical patient based on the positional coordinates of the at least one common surface landmark identified by the surface frame image module, positional coordinates of the surface frame within the first medical image, and positional coordinates of the surface frame within the second medical image.

2. The system of claim 1 further comprising a position sensor coupled to the surface frame;
   wherein the processor further comprises a frame tracking module that receives a signal output from the position sensor and determines a real-time location of the surface frame therefrom; and
   wherein the coregistration module is further programmed to dynamically adjust registration between the first medical image and the second medical image based on the real-time location of the surface frame.

3. The system of claim 1, wherein the surface frame image module is programmed with a pattern recognition algorithm that processes the acquired surface images to detect surface landmarks therein.

4. The system of claim 1, wherein the at least one common surface landmark comprises a micro feature located on the skin surface.

5. The system of claim 1, wherein the at least one common surface landmark comprises a body surface feature that is located proximate to and beneath the skin surface.

6. The system of claim 1, further comprising at least one of a radiopaque material and an oil-filled structure embedded within the surface frame.

7. The system of claim 1, wherein the surface detector assembly further comprises a visible grid positioned within the surface frame.

8. The system of claim 7, wherein the visible grid comprises one of a plurality of intersecting light beams and a plurality of radiopaque wires.

9. The system of claim 1, further comprising a handheld imaging probe having a probe camera coupled thereto, the probe camera configured to acquire surface images of a portion of the skin surface of the medical patient proximate the handheld imaging probe;
   wherein the processor further comprises:
   a tracking module for tracking the real-time position of the handheld imaging probe; and
   a probe surface image module connected to a signal output of the probe camera and programmed to identify positional coordinates of surface landmarks within the surface images acquired by the probe camera; and
   wherein the coregistration module is further programmed to:
   compare surface landmarks within at least one surface image acquired by the surface detector assembly with surface landmarks within at least one surface image acquired by the probe camera;
   identify at least one common surface landmark within the at least one surface image acquired by the surface detector assembly and the at least one surface image acquired by the probe camera based on the comparison; and
   co-register the first medical image with a medical image acquired using the handheld imaging probe based on positional coordinates of the at least one common surface landmark.

10. The system of claim 1, wherein at least one of the first medical images and the second medical image are acquired using a pair of mammographic compression pads; and wherein the surface detector assembly is integrated within the pair of mammographic compression pads.

11. A method of coregistering medical images comprising:
applying a surface detector assembly to a first skin surface of a medical patient, wherein the surface detector assembly comprises a surface frame detachably coupleable to the first skin surface and a camera system fixedly attached to the surface frame, the surface frame providing a frame of reference for the surface detector assembly to detect skin surface landmarks;
acquiring a first surface image of the first skin surface of the medical patient using the surface detector assembly;
determining positional coordinates of at least one surface landmark located within boundaries of the surface frame in the first surface image;
acquiring a first medical image of the medical patient having the surface frame depicted therein;
recording the medical images and positional coordinates of the surface frame as applied to the first skin surface of the medical patient;
applying the surface detector assembly to a second skin surface of the medical patient;
acquiring a second surface image of the second skin surface of the medical patient, the second skin surface at least partially overlapping the first skin surface;
determining positional coordinates of at least one surface landmark located within boundaries of the surface frame in the second surface image;
acquiring a second medical image of the medical patient having the surface frame depicted therein;
comparing the at least one surface landmark in the first surface image to the at least one surface landmark in the second surface image;
identifying at least one common surface landmark based on the comparison; and
coregistering the first medical image with the second medical image based on positional coordinates of the at least one common surface landmark.

12. The method of claim 11 further comprising acquiring the second surface image using the surface detector assembly.

13. The method of claim 11, further comprising determining the positional coordinates of the at least one surface landmark in the first surface image and the positional coordinates of the at least one surface landmark in the second surface image using a pattern recognition algorithm.

14. The method of claim 11 further comprising:
acquiring the first medical images using a first imaging modality; and
acquiring the second medical image using a second imaging modality, different from the first imaging modality.

15. The method of claim 11 further comprising:
acquiring the second medical image using an imaging system comprising a handheld probe; and
acquiring the second surface image using a camera coupled to the handheld imaging probe.

16. The method of claim 11, further comprising:
acquiring the second medical image using a pair of compression pads positioned on opposing surfaces of a breast of the medical patient; and
acquiring the second surface image using a camera system integrated within at least one of the compression pads of the pair of compression pads.

17. The method of claim 11, further comprising:
acquiring the first medical image with the surface frame located at a first position;
displaying the first position of the surface frame on a body diagram of the medical patient using positional data determined from the first medical image;
displaying a real-time position of the surface frame fitted with a position sensor on the body diagram of the medical patient prior to acquisition of the second medical image, wherein the real-time position of the surface frame is determined based on a signal output from the position sensor;
aligning the real-time position of the surface frame with the first position of the surface frame using the body diagram;
attaching the surface frame to the second skin surface of the medical patient at a second position that at least partially overlaps the first position;
acquiring the second surface image with the surface frame at the second position; and
acquiring the second medical image with the surface frame at the second position.

18. The method of claim 11 further comprising:
tracking motion of the medical patient during acquisition of the second medical images using a position sensor that monitors positional changes of the surface frame; and
dynamically adjusting registration between the first medical image and the second medical image based on the tracked motion.

19. A non-transitory computer readable storage medium having stored thereon instructions that cause a processor to:
access a first medical image of a medical patient having a first surface frame depicted at a first position on the medical patient;
access a first surface image acquired of a skin surface of the medical patient beneath the first surface frame;
detect surface landmarks located within the first surface frame within the first surface image;
access a second medical image of the medical patient having a second surface frame depicted at a second position on the medical patient, the second position at least partially overlapping the first position, wherein the second surface frame is different than the first;
access a second surface image acquired of the skin surface of the medical patient beneath the second surface frame;
detect surface landmarks located within the second surface frame within the second surface image;
compare the surface landmarks within the first surface landmarks within the second surface image;
identify at least one common surface landmark within the first surface image and the second surface image based on the comparison; and
coregister the first medical image with the second medical image based on positional coordinates of the at least one common surface landmark.

20. The system of claim 1 further comprising a display that displays the at least one common surface landmark relative to the surface frame on a body diagram of the medical patient.

21. The system of claim 20 wherein the display displays a real-time location of the surface frame on the body diagram.

* * * * *